United States Patent [19]
Pintauro et al.

[11] Patent Number: 5,989,288
[45] Date of Patent: *Nov. 23, 1999

[54] DEVICE FOR MAINTAINING URINARY CONTINENCE

[75] Inventors: William L. Pintauro, Ft. Lauderdale, Fla.; Rodney A. Brenneman, San Juan Capistrano, Calif.; Mario Maciel, Pinon Hills, Calif.; Sheila K. Wallin, Irvine, Calif.

[73] Assignee: Galt Laboratories, Inc., Irvine, Calif.

[ * ] Notice: This patent is subject to a terminal disclaimer.

[21] Appl. No.: 08/917,573

[22] Filed: Aug. 11, 1997

Related U.S. Application Data

[63] Continuation-in-part of application No. 08/696,333, Aug. 13, 1996, Pat. No. 5,782,916.
[51] Int. Cl.⁶ .................................. A61F 2/04; A61F 2/02
[52] U.S. Cl. ................................. 623/12; 623/11; 604/34; 600/29; 600/30
[58] Field of Search .......................... 623/12, 11; 604/34; 600/29, 30

[56] References Cited

U.S. PATENT DOCUMENTS

| | | |
|---|---|---|
| 2,638,093 | 5/1953 | Kulick . |
| 3,797,478 | 3/1974 | Walsh et al. . |
| 3,812,841 | 5/1974 | Isaacson . |
| 3,863,622 | 2/1975 | Buuck . |
| 3,939,821 | 2/1976 | Roth . |
| 4,197,835 | 4/1980 | Reinicke . |
| 4,204,282 | 5/1980 | Bolt . |
| 4,222,377 | 9/1980 | Burton . |
| 4,408,597 | 10/1983 | Teney, Jr. . |
| 4,551,862 | 11/1985 | Haber . |
| 4,587,955 | 5/1986 | Gengler . |
| 4,679,546 | 7/1987 | van Wallwijk van Doorn et al. . |
| 4,705,518 | 11/1987 | Baker et al. . |
| 4,716,901 | 1/1988 | Jackson et al. . |
| 4,731,083 | 3/1988 | Fischell . |
| 4,784,660 | 11/1988 | Fischell . |
| 4,832,680 | 5/1989 | Haber . |
| 4,846,784 | 7/1989 | Haber . |
| 4,850,963 | 7/1989 | Sparks . |
| 4,878,889 | 11/1989 | Polyak . |
| 4,968,294 | 11/1990 | Salama . |
| 4,974,811 | 12/1990 | Ishida ........................................ 604/34 |
| 4,994,019 | 2/1991 | Fernandez et al. . |
| 5,012,822 | 5/1991 | Schwarz ................................... 623/12 |
| 5,064,434 | 11/1991 | Haber . |
| 5,088,980 | 2/1992 | Leighton . |
| 5,097,848 | 3/1992 | Schwarz . |
| 5,123,428 | 6/1992 | Schwarz . |
| 5,140,999 | 8/1992 | Ardito . |
| 5,197,984 | 3/1993 | Kedem . |
| 5,437,604 | 8/1995 | Kulisz et al. . |
| 5,476,434 | 12/1995 | Kalb et al. . |
| 5,509,889 | 4/1996 | Kalb et al. . |
| 5,651,765 | 7/1997 | Schulman et al. ......................... 623/12 |
| 5,782,916 | 7/1998 | Pintauro et al. ............................. 623/1 |

OTHER PUBLICATIONS

J. Gundian et al., "Mayo Clinic Experience with the AS800 Artificial Urinary Sphincter . . . ", *Urology*, 41:318–321 (1993).

R. Janknegt et al., "Electrically stimulated gracilis sphincter for treatment of . . . ", *Lancet*, 340:1129–1130 (1992).

(List continued on next page.)

*Primary Examiner*—David H. Willse
*Assistant Examiner*—Suzette J. Jackson
*Attorney, Agent, or Firm*—Knobbe, Martens, Olson & Bear LLP

[57] ABSTRACT

A prosthetic device for controlling urinary continence is disclosed. The device has an opening pressure that varies in response to changes in physiologic parameters. The device can be controlled by the patient voluntarily without manual intervention. An introducer for transurethrally introducing the device is also disclosed. In addition, a nonsurgical or minimally invasive method of positioning the device for maintaining urinary continence is disclosed.

26 Claims, 31 Drawing Sheets

OTHER PUBLICATIONS

M.D. Craggs et al., "A preliminary report on a new hydraulic sphincter for . . . ", *Journal of Medical Engineering & Technology*, 15:58–62 (1991).

O. Lukkarinen, et al., "Treatment of Urinary Incontinence with an Implantable . . . ", *Scand J Urol Nephrol*, 23:85–88 (1989).

M. Abbar, et al., "Une revolution tranquille: l'endoprothese urethrale . . . " Progres en Urologie 3:771–777 (1993).

A. Gruneberger et al., "Entwicklung eines magnetischen Urethralverschlusses . . . " *Zentralblatt fur Gynakologie*, 115:328–331 (1993).

Summary of Dialog/Derwent World Pat. computer search, Mar. 17, 1995

Summary of Dialog/Medline/Biosis/SciSearch/Embase computer search, Mar. 17, 1995.

Preliminary Prospectus: UroMed Corporation, PaineWebber Incorporated Vector Securities International, Inc. Jan. 24, 1994.

Brochure: AMS Sphincter 800, Urinary Prothesis, Dry Facts of Incontinence Treatment, Pfizer American Medical Systems®, Jun. 1, 1991.

Brochure: HK Medical Technologies Incorporated, Autocath™100, 1994 Stanton, S. et al., "The Mechanism of Continence", Surgery of Female Incontinence, 2d Ed. pp. 1–21, 1986.

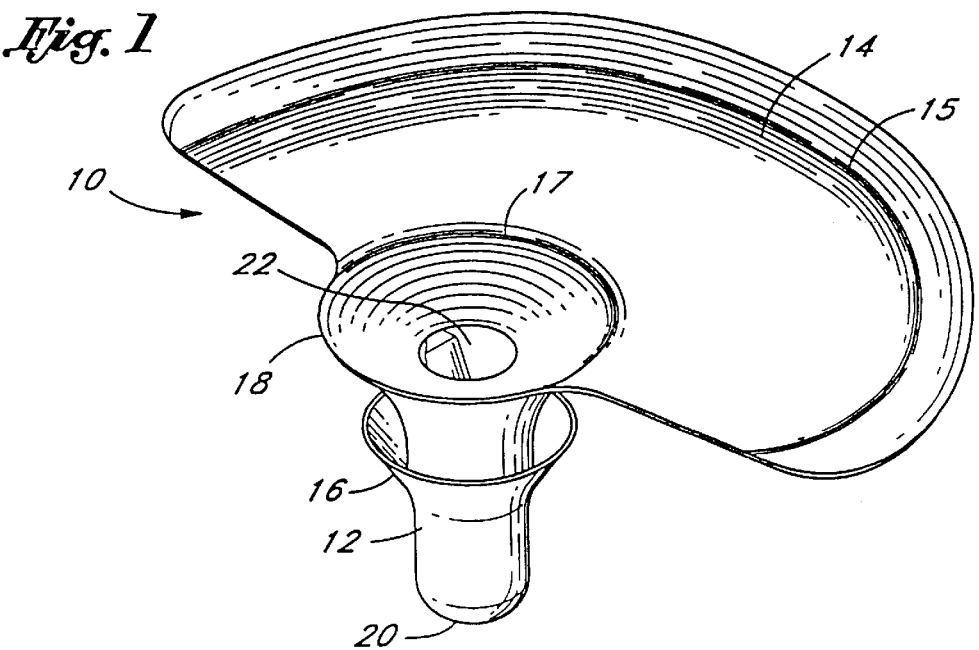
Fig. 1
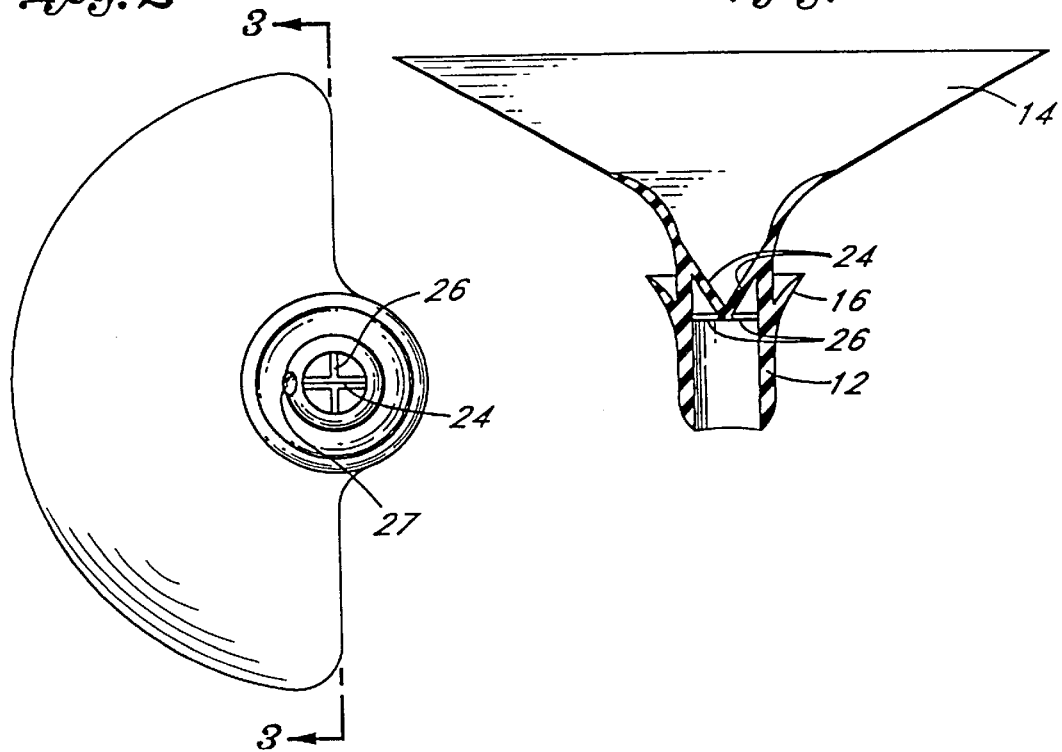
Fig. 2
Fig. 3

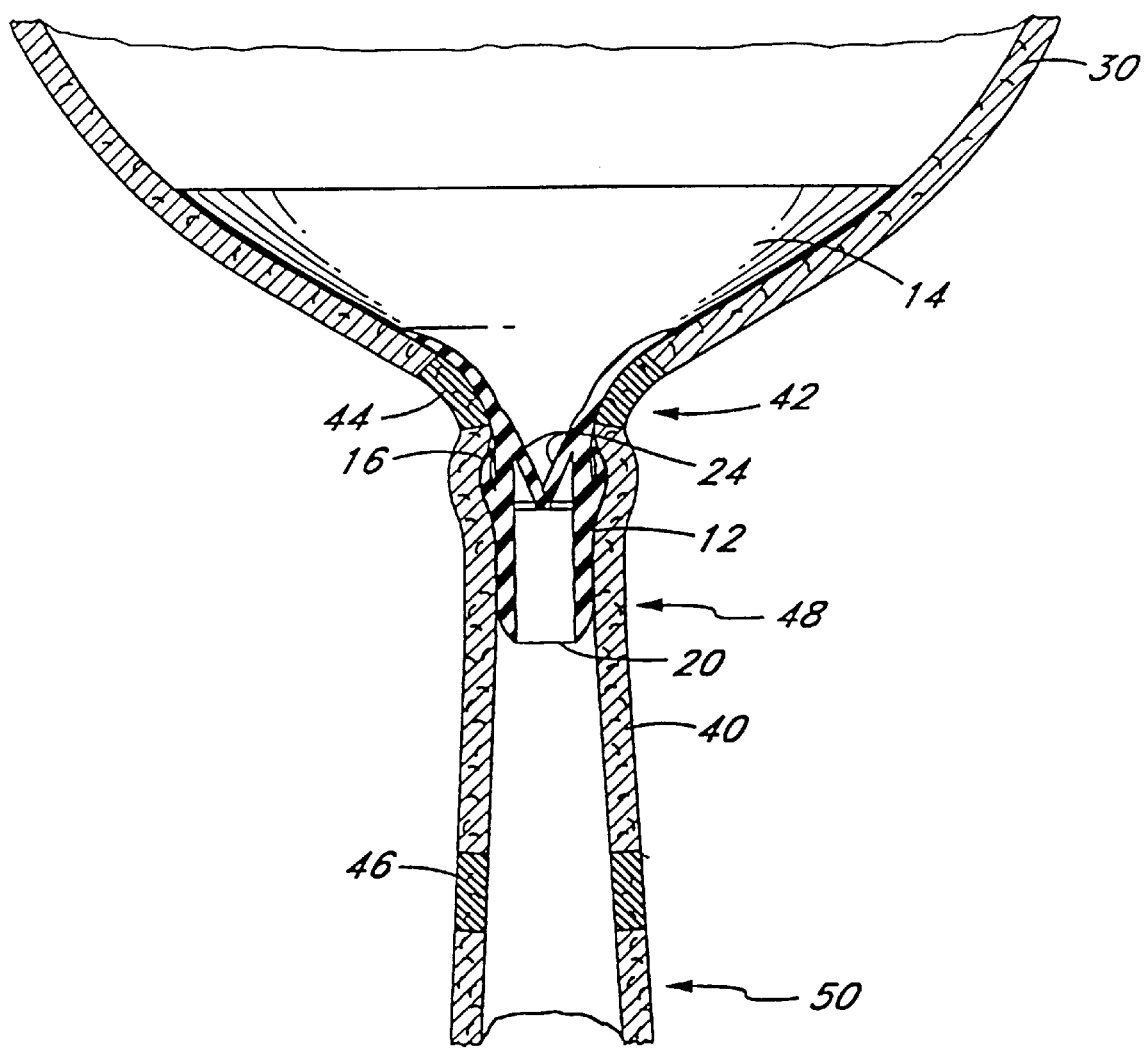

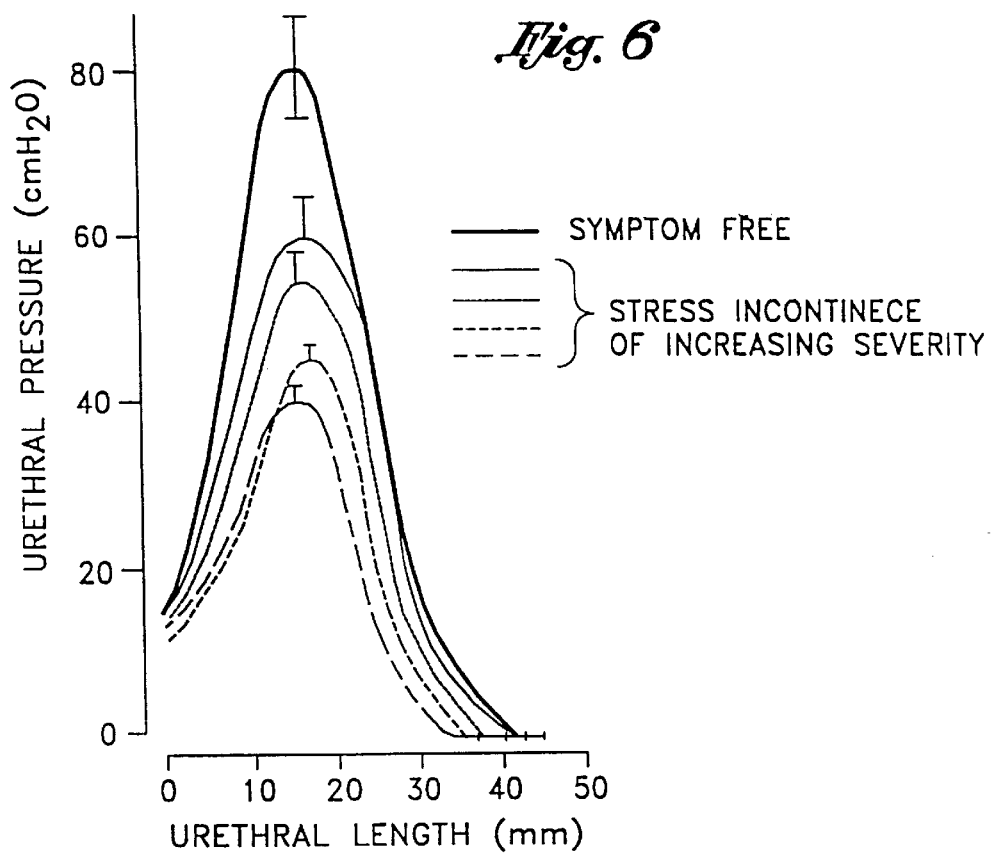
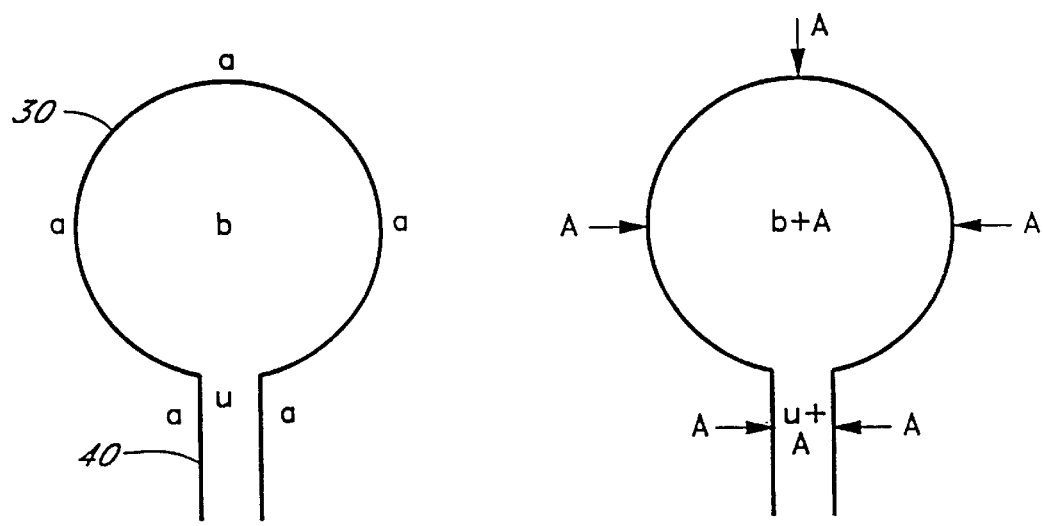

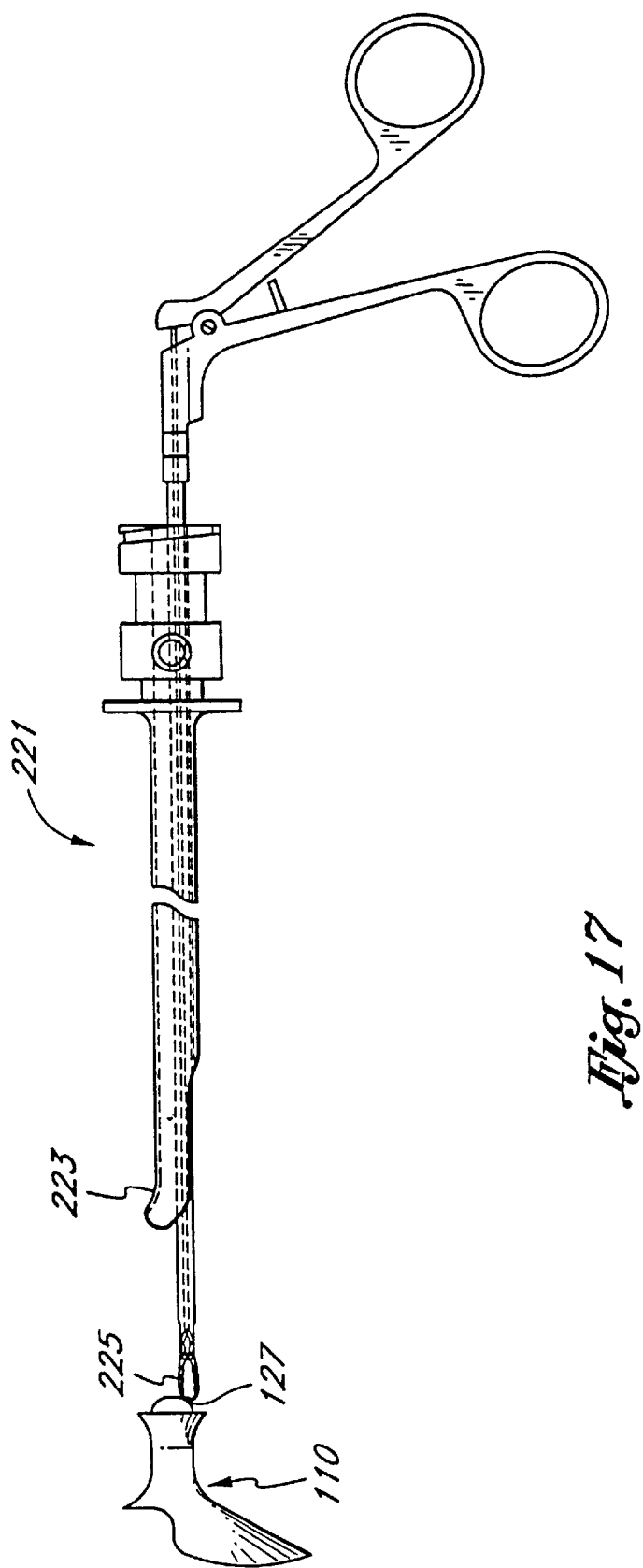

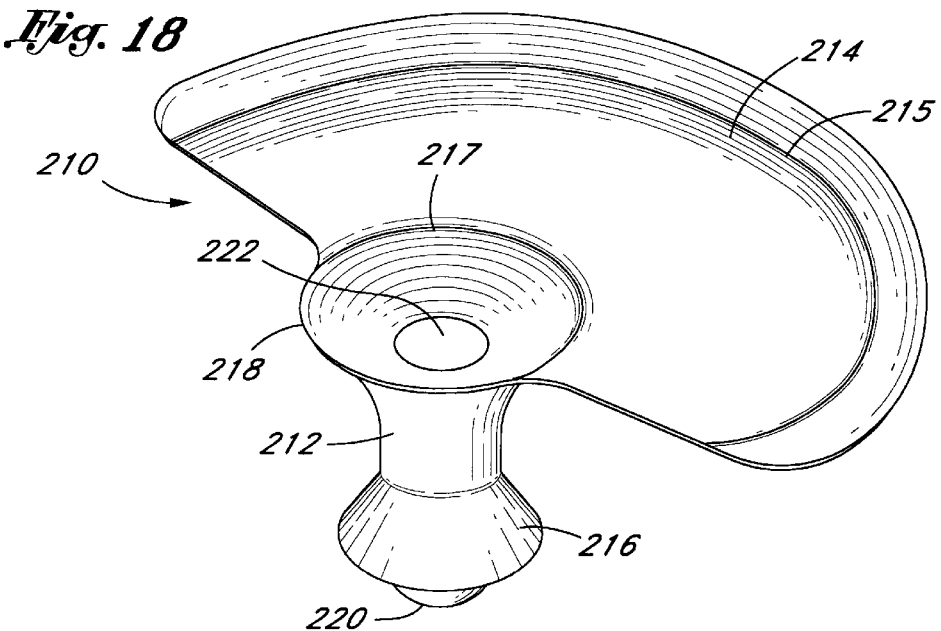
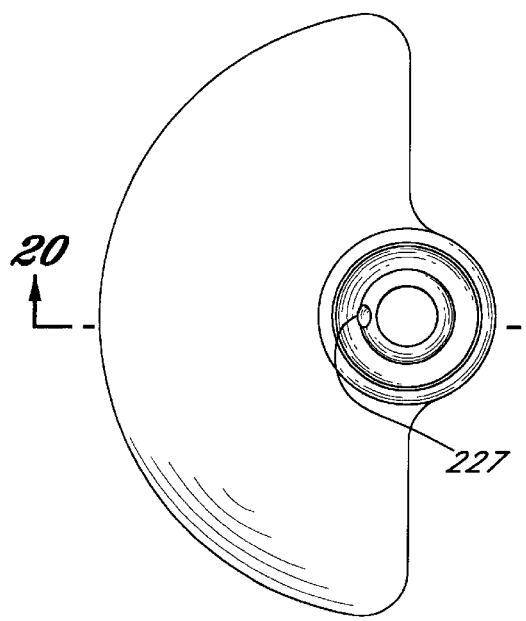
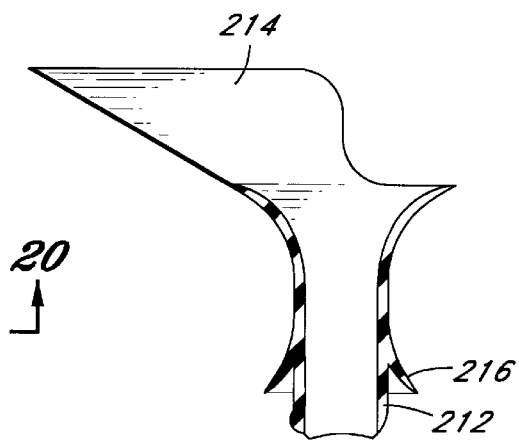

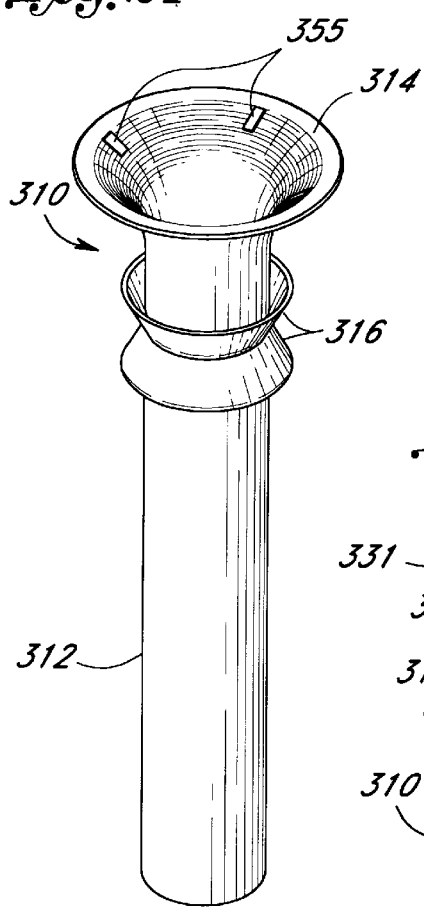
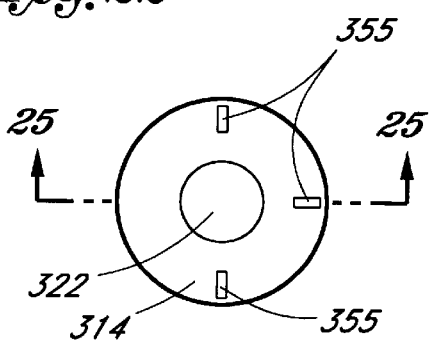
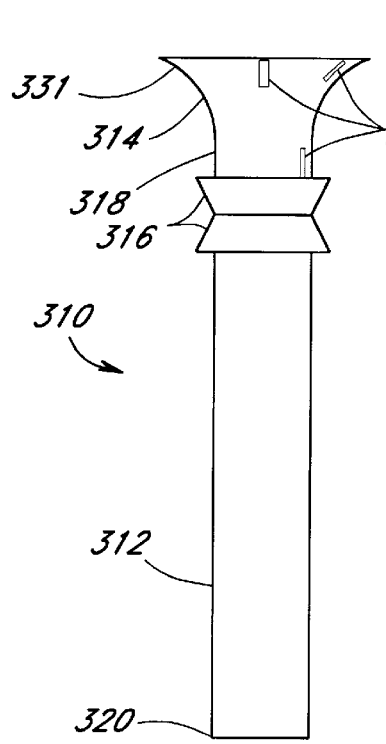
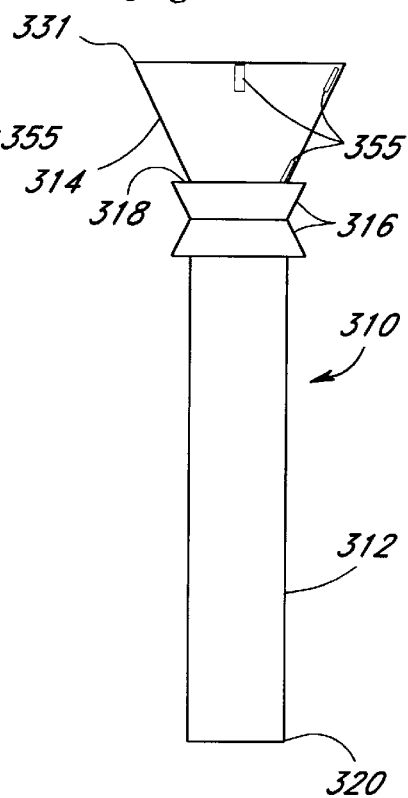
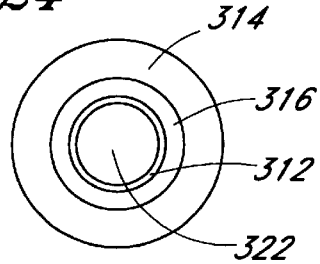

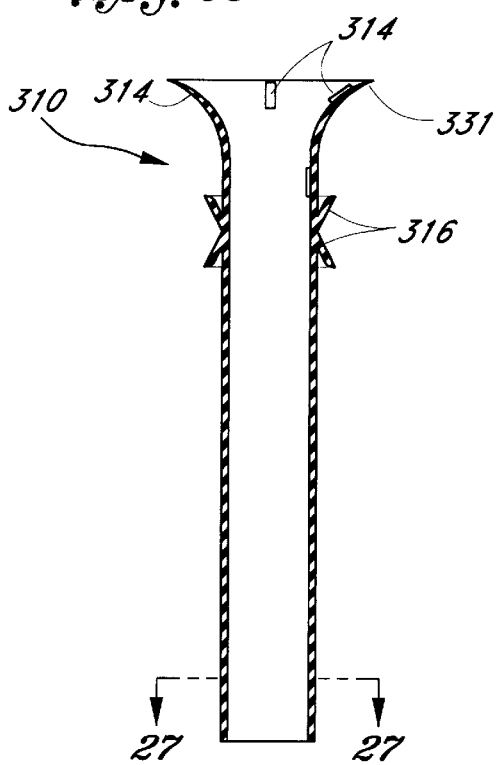
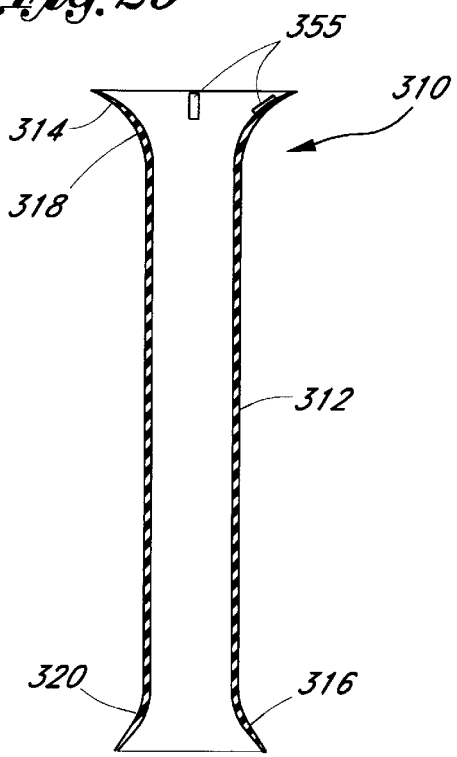
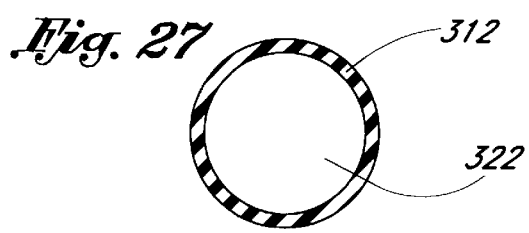
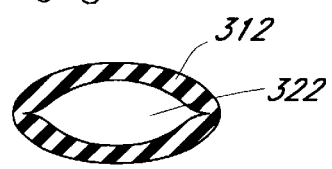
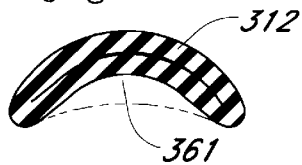
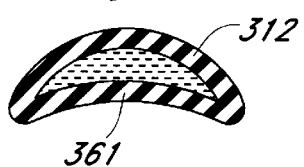

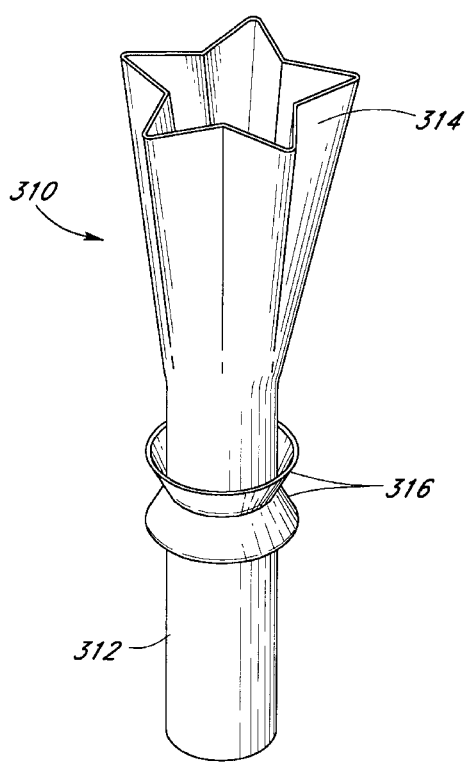
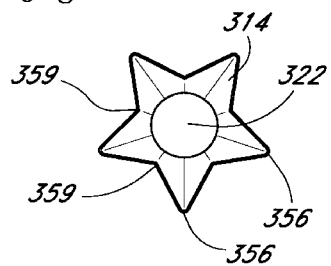
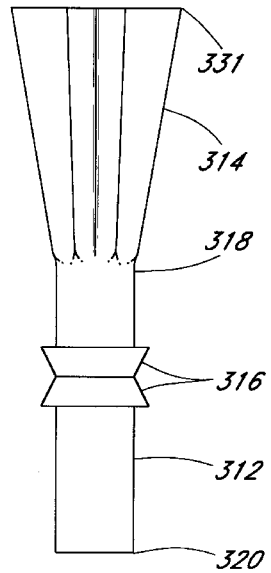
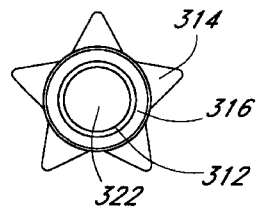

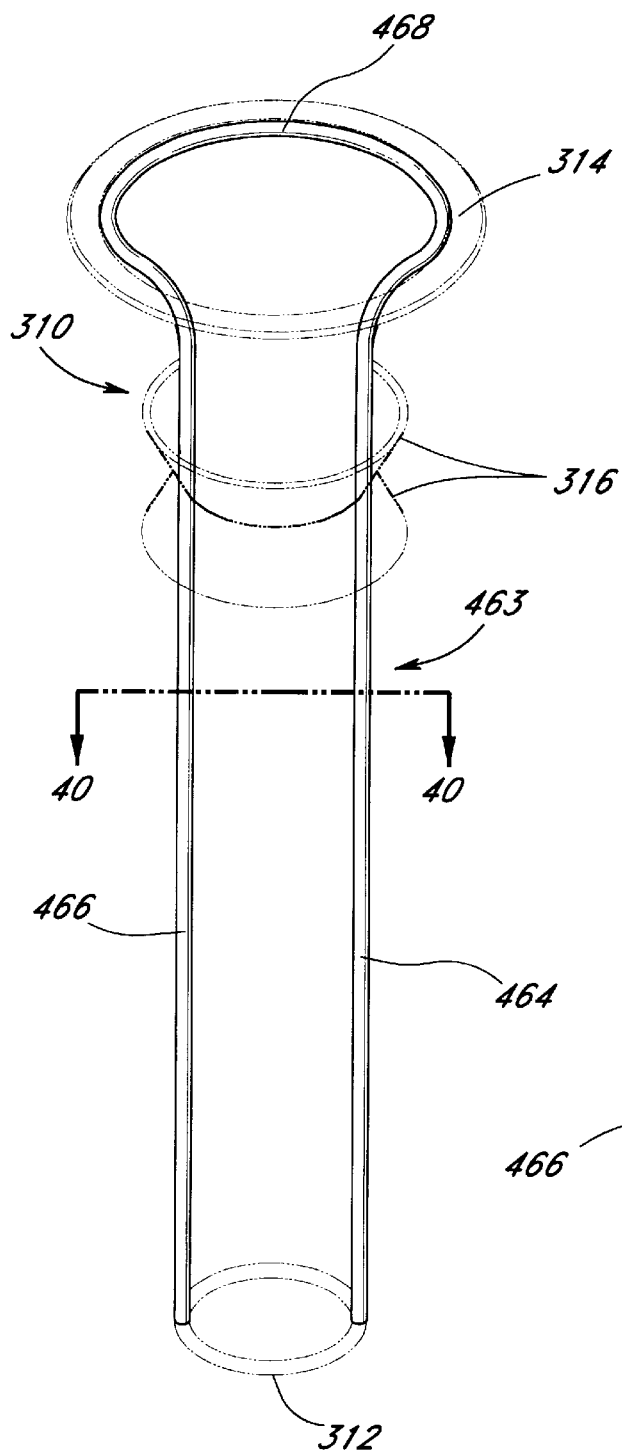

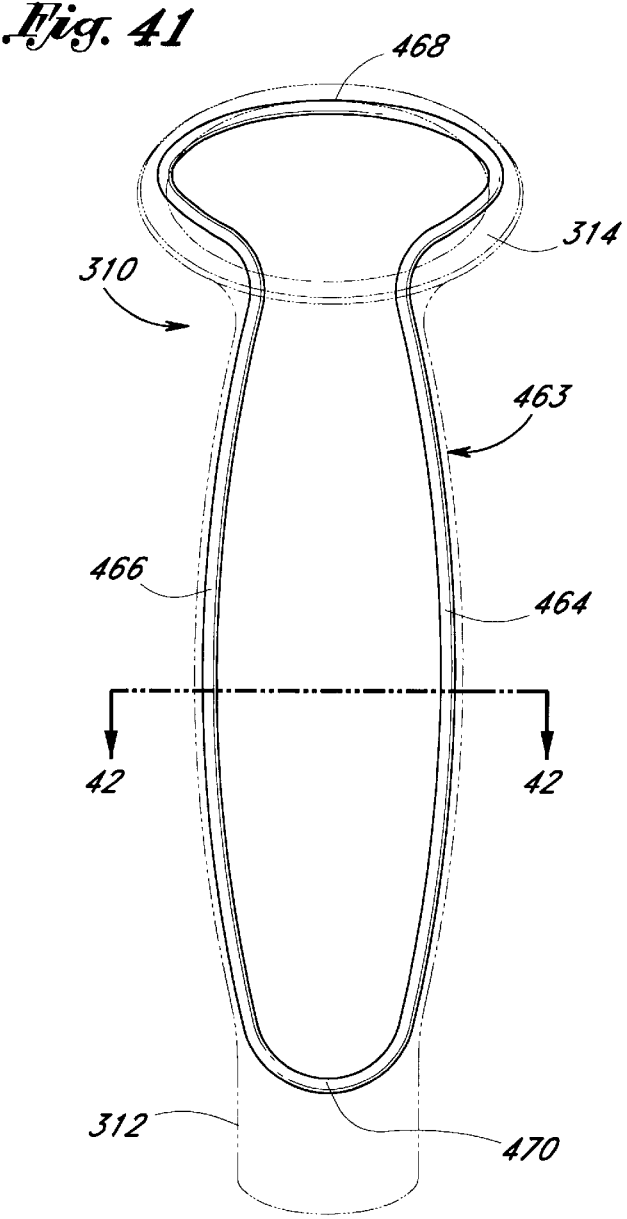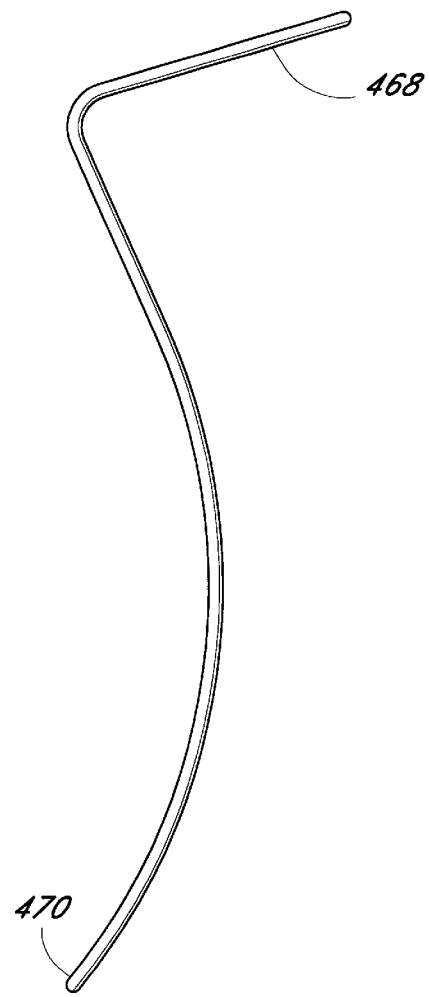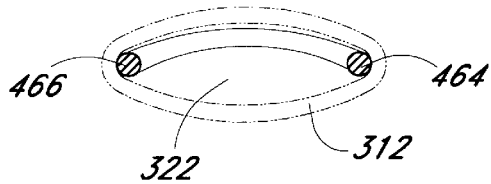

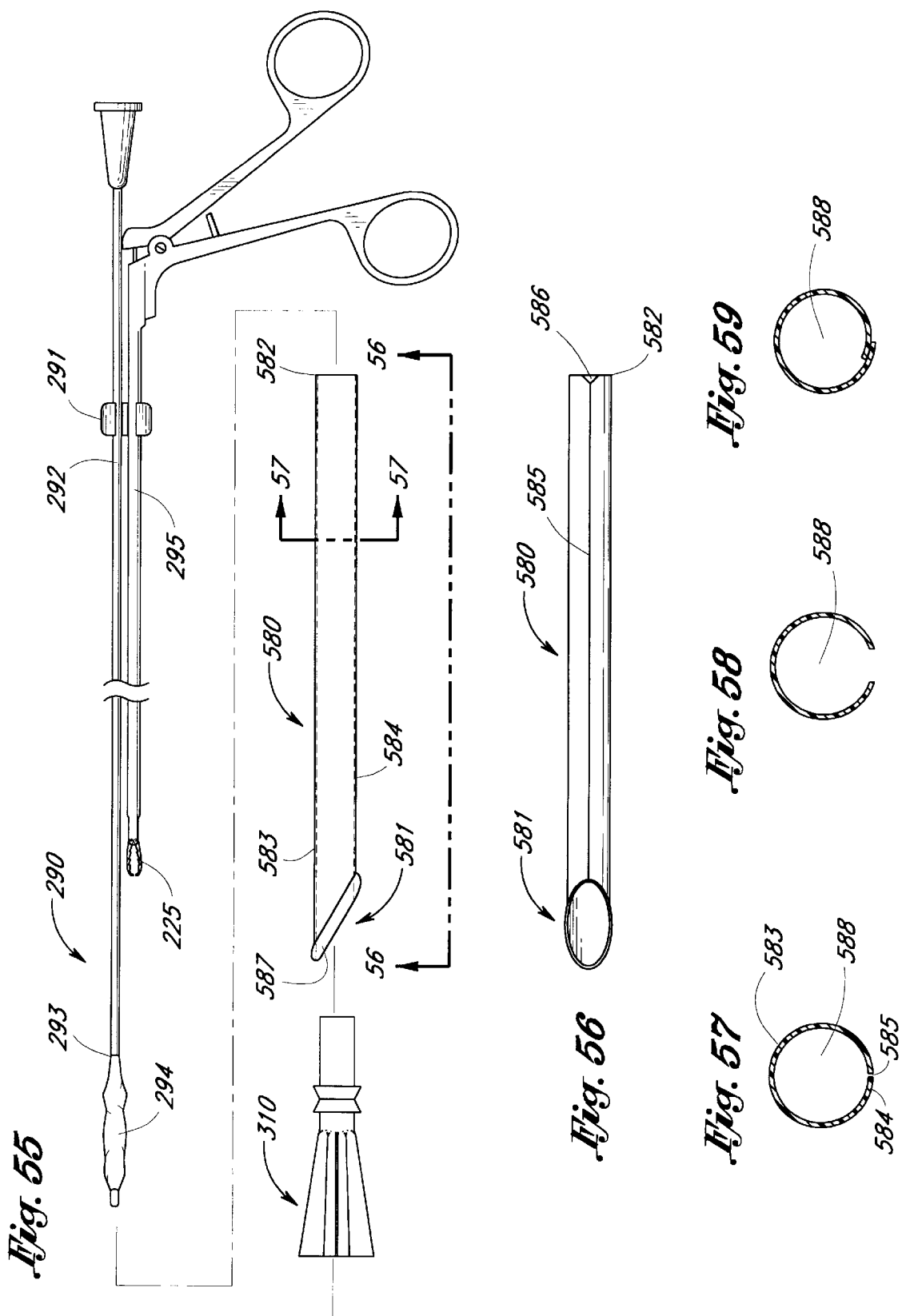

Fig. 66
Fig. 67
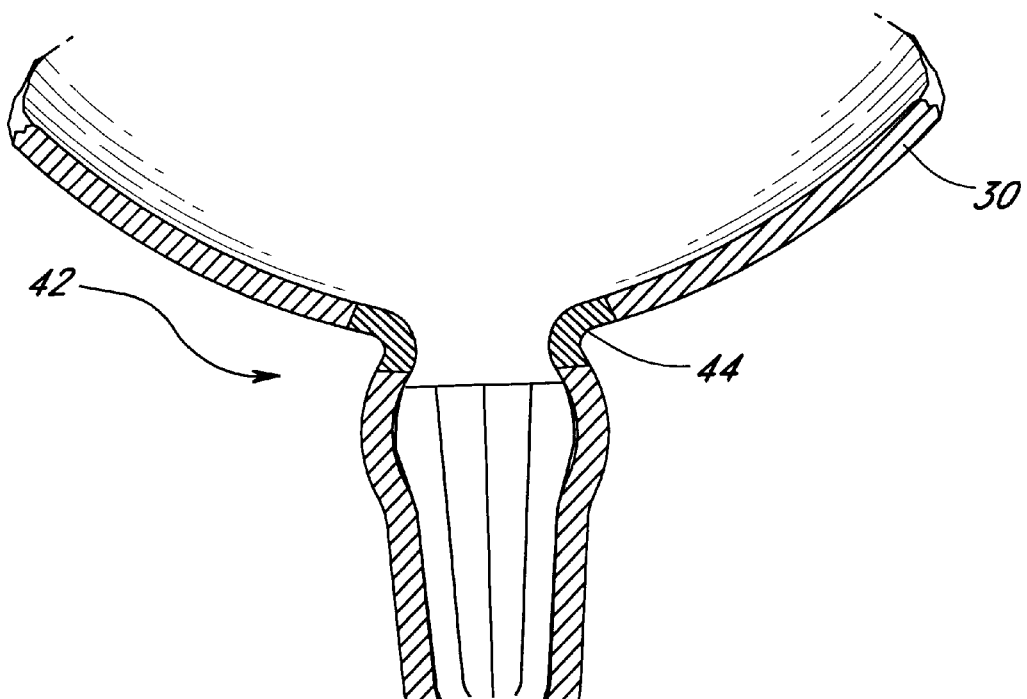
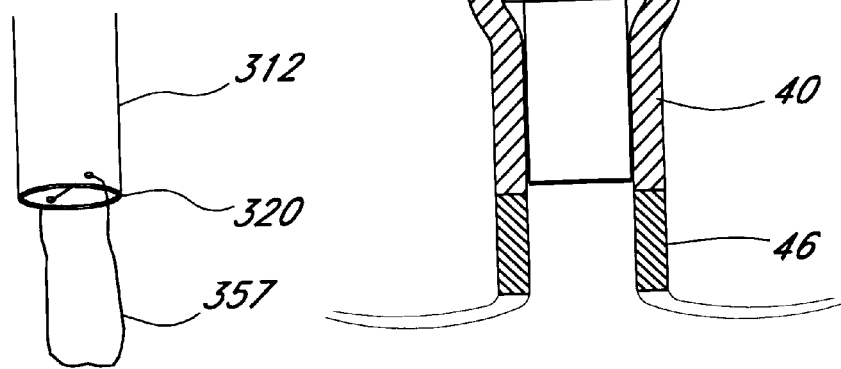

DEVICE FOR MAINTAINING URINARY CONTINENCE

This application is a continuation-in-part of U.S. application Ser. No. 08/696,333, filed Aug. 13, 1996, now U.S. Pat. No. 5,782,916 the disclosure of which is incorporated herein by reference.

FIELD OF THE INVENTION

The present invention relates to the field of prosthetic urethral valves or seals for controlling urinary continence. More particularly, the present invention relates to a prosthetic urethral device having an opening pressure that varies in response to changes in physiologic parameters. The present invention also relates to an introducer for transurethrally introducing the prosthetic device in a nonsurgical or minimally invasive procedure.

BACKGROUND OF THE INVENTION

Urinary incontinence is a widespread problem in the United States and throughout the world. Urinary incontinence affects people of all ages and can severally impact a patient both physiologically and psychologically. Urinary incontinence has a number of causes, including birth defects, disease, injury, aging, and urinary tract infection.

In light of the foregoing, a number of attempts have been made to combat urinary incontinence. One such attempt involves the use of a catheter connected to a collection bag with a clamping device on the catheter. Indwelling catheters, however, have a number of drawbacks. For instance, there is an infection risk associated with indwelling catheters, which provide a direct passage for bacteria or other microorganisms into the bladder. Thus, indwelling catheters can only be used for relatively short-term situations. In addition, indwelling catheters and associated collection bags are not cosmetically appealing to most patients.

Prosthetic urethral valves of the prior art for controlling incontinence also have numerous disadvantages. For instance, many prior art urethral valves utilize an inflatable cuff around the outside of the urethra. One disadvantage of such a valve is that it requires surgery for installation. In addition, such a valve must be operated externally and thus is dependent on manual intervention.

Intrauretheral valves of the prior art also generally require manual intervention. Another problem associated with intraurethral valves is that they may be displaced into the bladder or expelled from the urethra. There is also an infection risk associated with many such valves since they extend into the meatus and/or have portions of the device external to the urethra providing a passage for microorganisms into the bladder.

Thus, there remains a need for a nonsurgically installed prosthetic urethral valve or seal that responds to physiological conditions and thus can be controlled voluntarily by the patient without manual intervention.

SUMMARY OF THE INVENTION

In one aspect of the present invention, there is provided a prosthetic urethral valve assembly. The valve assembly includes a tubular body having a proximal end, a distal end, and a central lumen extending therethrough. Attached to the proximal end of the tubular body is a first anchor. The first anchor conforms to a portion of the base of the bladder so that the prosthetic urethral valve assembly remains properly located relative to the bladder and the urethra. The valve assembly also includes a second anchor, which is attached to the tubular body at a point between the proximal end and the distal end of the tubular body. The second anchor lies within the urethra and helps to anchor the valve assembly therein. The valve assembly also includes a valve, which can be located within the lumen of the tubular body between the proximal end and the distal end of the tubular body. When positioned in the patient, the distal end of the tubular body is disposed in the midurethra, such as between the internal urethral sphincter and the external urethral sphincter or introitus so that the opening pressure of the valve varies in response to changes in physiologic parameters.

Another aspect of the present invention relates to a method of maintaining urinary continence in a patient. The method includes positioning the prosthetic urethral valve assembly of the present invention in a patient so that the distal end of the tubular body and preferably the valve lie in the midurethra, such as between the internal urethral sphincter and the external urethral sphincter so that the opening pressure of the valve varies in response to changes in physiologic parameters. For example, the opening pressure of the valve can vary in response to pressure exerted on the urethra caused by a rise in abdominal pressure.

Another aspect of the present invention relates to a method of varying the opening pressure of a prosthetic urethral valve in response to changes in abdominal pressure. The method includes providing a prosthetic urethral valve having a proximal end, a distal end, and a valved flow path therebetween. The valve is positioned in a patient within the flow path between the bladder and the outside of the patient. Preferably, the valve is positioned in the patient within the urethra between the internal sphincter and the external sphincter. The method also includes exposing the distal side of the valve to elevations in intraabdominal pressure and increasing the opening pressure of the valve in response to elevations in intraabdominal pressure.

In accordance with another aspect of the present invention, there is provided an intraurethral device for maintaining urinary continence. The device in accordance with this aspect of the present invention is preferably valveless. The device includes a tubular body having a proximal end, a distal end, and a central lumen extending therethrough. Attached to the proximal end of the tubular body is a first anchor, which conforms to a portion of the base of the bladder so that the device remains properly located relative to the bladder and the urethra. The device is made of a substantially compliant material so that the tubular body of the device reversibly seals in response to internal forces affecting the urethra and bladder neck. For instance, when micturition is undesired, the tubular body of the device reversibly seals in response to inwardly directed urethral forces, thereby maintaining urinary continence. The tubular body of the device can also reversibly seal by kinking in response to rotational descent of the bladder neck and urethra, thereby maintaining continence, such as in patients suffering from incontinence caused by hypermobility and/or weak pelvic floor muscles.

Another aspect of the present invention relates to an alternate embodiment of the intraurethral device for maintaining urinary continence. The device includes a tubular body having a proximal end, a distal end, and a central lumen extending therethrough. The tubular body has a shape which conforms to the urethra. The device also includes a first anchor which is attached to the tubular body. The first anchor is preferably attached to the proximal end of the tubular body. The first anchor conforms to a portion of the urethra, preferably the proximal urethra, to resist migration of the intraurethral device relative to the urethra. The device may also include a second anchor attached to the tubular body. The device is made of a substantially compliant material so that portions of the device, such as the tubular body and/or first anchor, reversibly seal in response to anatomical forces affecting the urethra and bladder neck.

In accordance with another aspect of the present invention there is provided a combination of a device for treating urinary incontinence and an introducer for transurethrally introducing the device. The introducer is an elongate generally tubular structure having a first end, a second end, and a central lumen extending therethrough. The tubular structure preferably has a variable diameter. The variable diameter feature of the tubular structure may be accomplished by providing the wall of the tubular structure with a longitudinally extending split. The split may extend partially or fully along the length of the wall of the tubular structure. The variable diameter of the tubular structure allows expansion of the tubular structure to facilitate loading and deployment of the device. The variable diameter of the tubular structure also allows contraction of the tubular structure during transurethral introduction of the device to minimize urethral trauma and patient discomfort.

Another aspect of the present invention relates to a method of maintaining urinary continence in a patient. The method involves using an introducer to transurethrally introduce a device for maintaining urinary continence which is made of a substantially compliant material so that the device reversibly seals in response to anatomical forces affecting the urethra and bladder neck. The device for maintaining urinary continence can be provided to the physician in a variety of lengths so that the physician can choose an appropriate device for a given patient. If necessary, the device can also be cut to length by the physician based on the patient's measured urethral length. Preferably, the length of the device is less than the patient's urethral length. After loading the device into the introducer, the physician inserts the loaded introducer into the urethra so that a first end of the introducer extends into the bladder. The device is then displaced out of the introducer and into the bladder. The physician then withdraws the introducer from the patient and withdraws the device until the device is positioned within the flow path between the bladder and introitus, thereby maintaining urinary continence. Preferably, the device is withdrawn until the entire device is positioned within the urethra. The introducer used in accordance with this method may also include a generally tubular structure having a variable diameter. In such cases, the tubular structure can be expanded to increase the diameter of the introducer to facilitate loading and displacement of the device for maintaining urinary continence. The tubular structure can also be contracted to decrease the diameter of the introducer, such as during transurethral insertion of the loaded introducer to minimize urethral trauma and patient discomfort.

In accordance with another aspect of the present invention, there is provided a method of positioning a device for maintaining urinary incontinence in a patient. The device for maintaining urinary continence is coupled to a locating device having an expandable tip, such as a balloon catheter, so that the proximal end of the device for maintaining urinary continence is separated a preselected distance from the expandable tip of the locating device. The coupled device for maintaining urinary continence and locating device is transurethrally introduced so that at least the expandable tip of the locating device extends into the bladder. The expandable tip of the locating device is then expanded from a non-expanded configuration to an expanded configuration. The coupled device for maintaining urinary continence and locating device is then withdrawn until the expanded tip of the locating device contacts the bladder neck so that the device for maintaining urinary continence is properly positioned within the urinary tract. The expandable tip is then returned to the non-expanded configuration, the device for maintaining urinary continence is decoupled from the locating device, and the locating device is removed from the patient, leaving the device for maintaining urinary continence properly positioned within the urinary tract of the patient.

BRIEF DESCRIPTION OF THE DRAWINGS

FIG. 1 is a perspective view of one embodiment of the prosthetic urethral valve according to the present invention.

FIG. 2 is a bottom view of the valve depicted in FIG. 1.

FIG. 3 is an elevational cross-sectional view taken along line 3—3 of FIG. 2.

FIG. 5 is an elevational cross-sectional view taken along line 5—5 of FIG. 4.

FIG. 6 graphically depicts the relationship between urethral pressure and urethral length in a group of symptom-free women and four groups with stress incontinence of varying severity.

FIGS. 7A and 7B diagrammatically represent the bladder, the urethra, and various pressures relating to urinary tract physiology.

FIG. 17 is a side view of the grasping forceps extending distally from the cystoscope to releasably engage the prosthetic urethral valve of the present invention.

FIG. 18 is a perspective view of an alternate embodiment of the device according to the present invention.

FIG. 19 is a bottom view of the embodiment depicted in FIG. 18.

FIG. 20 is an elevated cross-sectional view taken along line 20—20 of FIG. 19.

FIG. 21 is a perspective view of an alternate embodiment of the device according to the present invention.

FIG. 22 is a top view of the embodiment depicted in FIG. 21.

FIG. 23 is an elevational side view of the embodiment depicted in FIG. 21.

FIG. 23A is an elevational side view of an alternate embodiment of the device depicted in FIG. 23.

FIG. 24 is a bottom view of the embodiment depicted in FIG. 21.

FIG. 25 is a cross-sectional view taken along line 25—25 of FIG. 22.

FIG. 26 is a cross-sectional view of an alternate embodiment of the device illustrated in FIG. 25.

FIG. 27 is a cross-sectional view taken along line 27—27 of FIG. 25.

FIG. 28 is a cross-sectional view of an alternate embodiment of the device illustrated in FIG. 25 showing an alternate shaped tubular body.

FIG. 29 is a cross-sectional view of an alternate embodiment of the device illustrated in FIG. 25 showing an alternate shaped tubular body.

FIG. 30 is a cross-sectional view of an alternate embodiment of the device illustrated in FIG. 25 showing an alternate shaped and variable stiffness tubular body in a closed position.

FIG. 31 is a cross-sectional view of an alternate embodiment of the device illustrated in FIG. 25 showing an alternate shaped and variable stiffness tubular body in an open position.

FIG. 35 is a perspective view of an alternate embodiment of the device according to the present invention.

FIG. 36 is a top view of the embodiment depicted in FIG. 35.

FIG. 37 is an elevational side view of the embodiment depicted in FIG. 35.

FIG. 38 is a bottom view of the embodiment depicted in FIG. 35.

FIG. 39 is a frontal perspective view of an alternate embodiment of the present invention showing a resilient support structure embedded in a device which is shown in phantom.

FIG. 40 is a cross-sectional view taken along line 40—40 of FIG. 39.

FIG. 41 is a frontal perspective view of an alternate embodiment of the present invention showing a resilient support structure inserted in the lumen of a device which is shown in phantom.

FIG. 42 is a cross-sectional view taken along line 42—42 of FIG. 41.

FIG. 43 is a side view of the resilient support structure depicted in FIG. 41.

FIG. 55 is an exploded side view showing a device for maintaining urinary continence, an introducer, and a balloon catheter coupled to grasping forceps.

FIG. 56 is a bottom view of the introducer taken along line 56—56 of FIG. 55.

FIG. 57 is a cross-sectional view of the introducer taken along line 57—57 of FIG. 55.

FIG. 58 is a schematic cross-sectional view showing the introducer in an expanded configuration.

FIG. 59 is a schematic cross-sectional view showing the introducer in a contracted or overlapping configuration.

FIG. 66 is a schematic cross-sectional view showing the device for maintaining urinary continence positioned in the urinary tract of the patient.

FIG. 67 is a perspective end view showing a tether attached to the distal end of a tubular body of the device for maintaining urinary continence.

DETAILED DESCRIPTION OF THE PREFERRED EMBODIMENT

Figure 4:
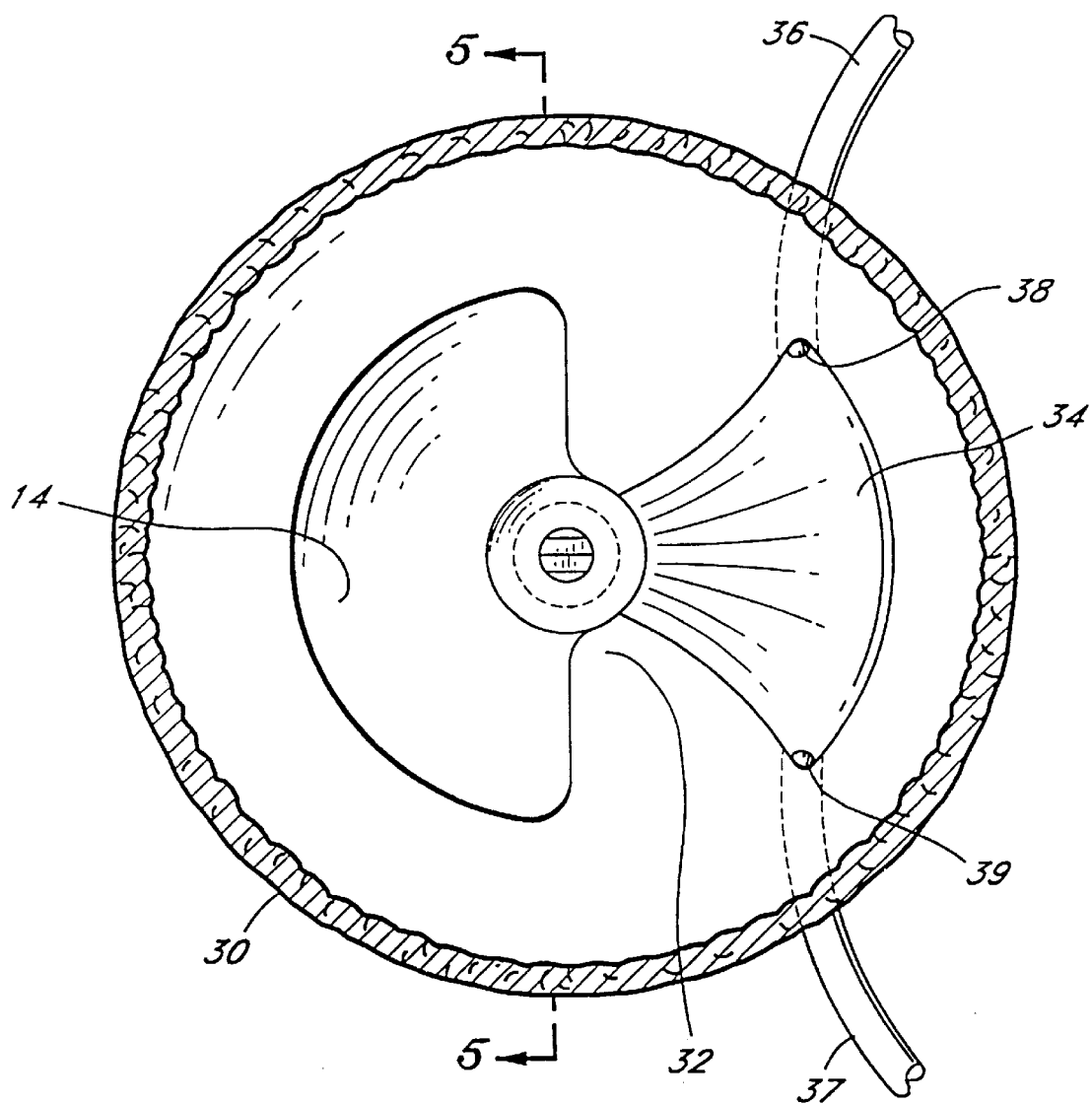
FIG. 4 is a transverse cross-sectional view through the bladder showing a top view of the device positioned in the bladder.

Referring to FIG. 1, there is disclosed a perspective view of the prosthetic urethral valve assembly 10 of the present invention. The valve assembly includes a tubular body 12 having a proximal end 18, a distal end 20, and a central lumen 22 extending therethrough. As illustrated in FIG. 2, a gripping tab or boss 27 is preferably included at the distal end 20 of tubular body 12 to facilitate transurethral placement of the valve, which is discussed in more detail below.

The valve assembly 10 also includes a first anchor 14. The first anchor preferably conforms to a portion of a base 32 of a bladder 30 as illustrated in FIGS. 4 and 5. The first anchor 14 functions to releasably secure the valve assembly 10 relative to the bladder 30 and the urethra 40, while preferably avoiding contact with the trigone 34 of the bladder 30. The first anchor 14 also helps prevent urine from escaping around the exterior of the device.

The trigone 34, illustrated in FIG. 4, is a triangular area of the bladder located between the urethra 40 and the two ureteric orifices 38 and 39. The ureteric orifices 38 and 39 drain urine from the ureters 36 and 37, respectively. Minimizing or avoiding contact between the first anchor 14 and the trigone 34 is desirable because the trigone contains a nerve bed which can be stimulated by tactile means resulting in an undesirable sense of urinary urgency.

In light of the foregoing considerations, the first anchor is preferably an atraumatic retention structure which is enlargeable from a first, collapsed configuration for transurethral placement to a second, enlarged configuration for resisting distal migration out of the bladder and into the urethra. In the illustrated embodiment, the first anchor comprises a pliable semiconical retention flap that inclines generally radially outwardly in the proximal direction from the proximal end 18 of the tubular body 12 as illustrated in FIG. 1. The retention flap is mechanically biased in the direction of the second, enlarged configuration as illustrated to help prevent the valve assembly 10 from being expelled distally from the urethra 40. The proximal surface of the first anchor 14 is exposed to the intravesical pressure of the bladder, which helps prevent the valve assembly 10 from being dislodged proximally into the central portion of the bladder.

In most patients, the trigone extends circumferentially approximately 60° to 90°. Thus, if properly placed within the bladder, the first anchor 14 can extend circumferentially up to as much as from approximately 270° to 300° and still avoid contacting the trigone. Preferably, the first anchor extends circumferentially either continuously or intermittently through an angle of approximately 100° to 180° in order to account for potential human error during placement, yet still provide an adequate surface area to achieve the anchoring function described above. In some embodiments, the construction material of the first anchor 14 is such that the anchoring function can be achieved with circumferential extension of less than about 100°.

A number of structures can be used to minimize either the circumference or the total contact area of the first anchor 14 yet still provide for adequate anchoring. For example, circumferentially extending reinforcing rings 15 and/or 17, such as a fine gauge spring wire may be incorporated into the valve assembly. The use of spring wires would provide a bias in the direction of the second, enlarged configuration while permitting a reduction in the size and mass of the anchor. Spring wires can alternatively extend in planes that are generally parallel to the longitudinal axis of the tubular body 12. Wires can be integrally molded into the anchor 14. Spring bias can also be optimized simply by adjusting the wall thickness of the anchor 14 and through appropriate materials choice.

In addition, as will be apparent to one of ordinary skill in the art, a variety of other structures could be used to accomplish the function of first anchor 14. For instance, the first anchor 14 may comprise a series of discontinuous, mechanically biased flexible struts extending from the proximal end 18 of the tubular body 12. Typically, two or three or more struts would be used. Alternatively, spring biased hinged anchors could be used to releasably secure the valve assembly 10 relative to the bladder 30 and the urethra 40.

In addition to the first anchor 14, preferably the valve assembly 10 also includes a second anchor 16. The second anchor 16 also helps to releasably secure the valve assembly 10 relative to the bladder 30 and the urethra 40. In addition, the second anchor 16 helps to stabilize the tubular body 12 within the urethra, especially in a patient having a large diameter urethra.

In the illustrated embodiment, the second anchor 16 is an annular flange attached to the tubular body 12 at a point between the proximal end 18 and the distal end 20. As illustrated in FIG. 1, the second anchor ramps radially outwardly in the proximal direction, thereby providing a mechanical bias against proximal dislodgement of the tubular body into the bladder. Optionally, one or more nitinol rings can be molded into the annular flange. After insertion of the valve assembly, expansion of the nitinol rings or other resilient support structures in response to body temperature provides an additional mechanical bias to help further secure the valve assembly.

As will be apparent to one of ordinary skill in the art, a variety of structures other than the proximally extending annular flange described above could be used to accomplish the function of second anchor 16. For instance, a variety of radially extending preferably atraumatic structures, such as semi-spheres, ridges or barbs can be attached to or integrally molded with the tubular body 12. Proximally and/or distally extending suture ends attached to the tubular body 12 using well known methods can also be used to accomplish the function of the second anchor 16.

The valve assembly 10 also includes a valve 24, such as a duckbill valve, which is preferably located within the fluid flow path through tubular body 12 between the proximal end 18 and the distal end 20. As illustrated in FIG. 3, optional valve supports 26 can also be included in the present invention to increase the opening pressure of the valve, if necessary, based on the characteristics of the material and dimensions used to construct the valve assembly 10.

The function of the valve is to assist normal physiological mechanisms to regulate the flow of urine through the tubular body 12. When the valve 24 is in an open position, the tubular body provides a fluid communication path between the bladder 30 and the urethra 40. When the valve is in the open position, preferably a flow rate of approximately 5–15 cc per second is achieved when the pressure differential on the valve is between approximately 20–30 $cmH_2O$. When the valve is in a closed position, the valve assembly 10 provides a seal preventing incontinence.

Figure 49:
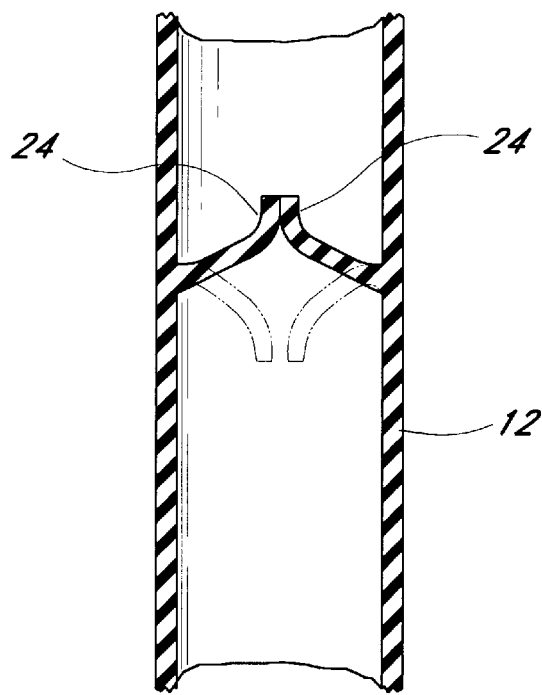
FIG. 49 is a schematic elevational cross-sectional view showing a collapsible duckbill valve in a closed position. The open position of the valve is shown in phantom.

A variety of structures other than the duck bill valve described above could be used to accomplish the function of the valve 24. For instance, the valve 24 could comprise a collapsible duckbill valve such as that illustrated in FIG. 49. In FIG. 49, the valve 24 is shown in both the open and closed positions, the open position being shown in phantom. One advantage of the valve 24 illustrated in FIG. 49 is that it has a relatively high opening pressure above which little resistance to flow is encountered.

Figure 50:
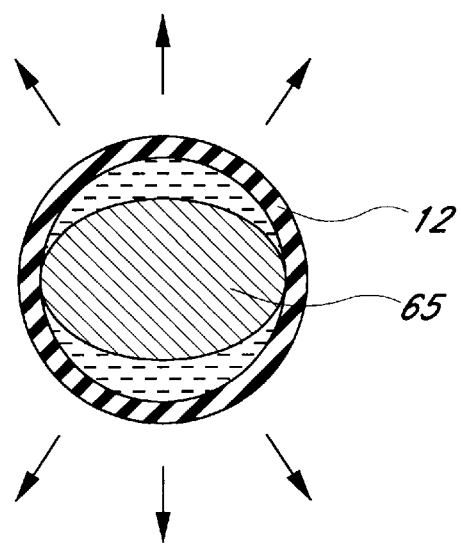
FIG. 50 is a schematic cross-sectional view showing an alternate embodiment of a valve-like structure of the present invention in an open position.
Figure 51:
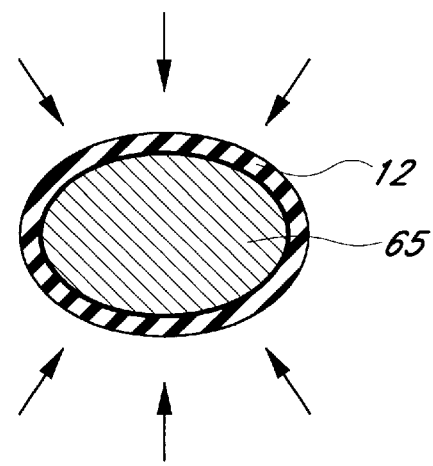
FIG. 51 is a schematic cross-sectional view showing the valve-like structure of FIG. 50 in a closed position.

In addition, a valve-like function could be achieved as illustrated in FIGS. 50–51 in which a solid rod-like structure 65 is placed within the tubular body 12. The rod-like structure 65 is preferably oval as illustrated in FIGS. 50–51. In its open state, the diameter of the tubular body 12 is larger than that of the rod 65. Using conventional techniques such as thermal bonding, solvent bonding or suitable adhesives known in the art, the tubular body 12 is secured to the rod 65 preferably along the length of the rod 65 at least two points as illustrated in FIG. 50.

During bladder filling, the urethra exerts radially inwardly directed forces on the tubular body 12 which keep the tubular body 12 sealed against the rod 65 as illustrated in FIG. 51, thereby maintaining continence. During micturition, however, the pressure exerted by the urethra decreases allowing radial expansion of the tubular body 12 to its open position as illustrated in FIG. 50.

Figure 52:
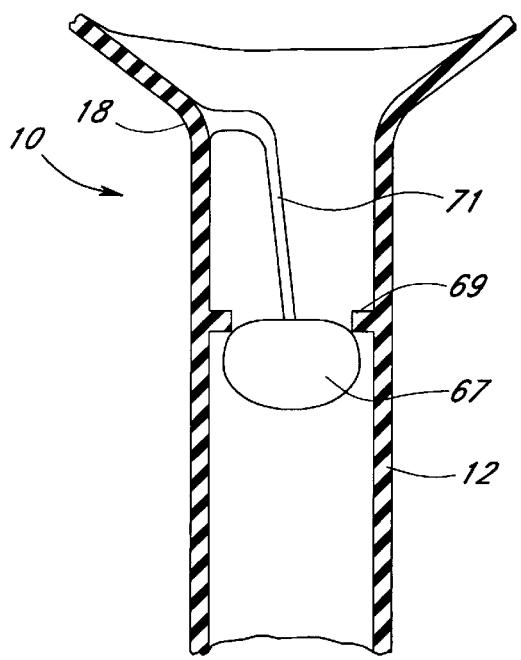
FIG. 52 is a schematic elevational cross-sectional view showing a tethered ball type valve in a closed position.
Figure 53:
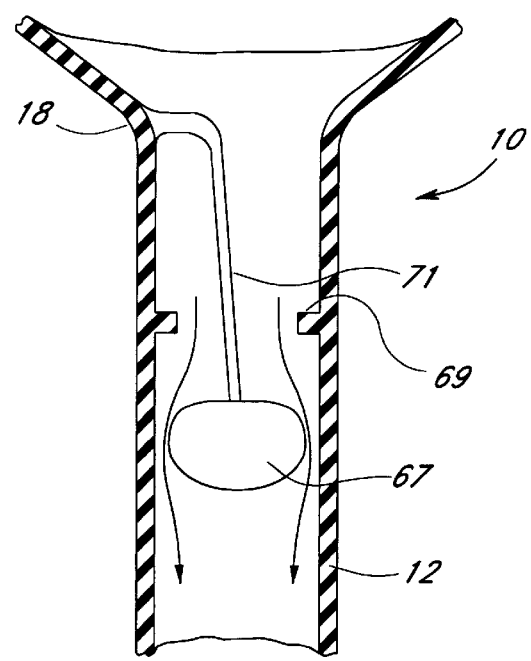
FIG. 53 shows the valve of FIG. 52 in an open position.

The function of the valve 24 could also be accomplished using a tethered ball type valve as illustrated in FIGS. 52–53. When the valve is in the closed position, the ball portion 67 of the valve preferably rests against an inwardly projecting extension 69 of the tubular body 12 as illustrated in FIG. 52. The ball portion 67 of the valve is attached to an elastomeric tether 71. As will be apparent to one of ordinary skill in the art, the tether 71 can be attached at a variety of places on the valve assembly 10, such as the proximal end 18 of the tubular body 12 as illustrated in FIGS. 52–53. FIG. 53 shows the valve in the open position.

Figure 54:
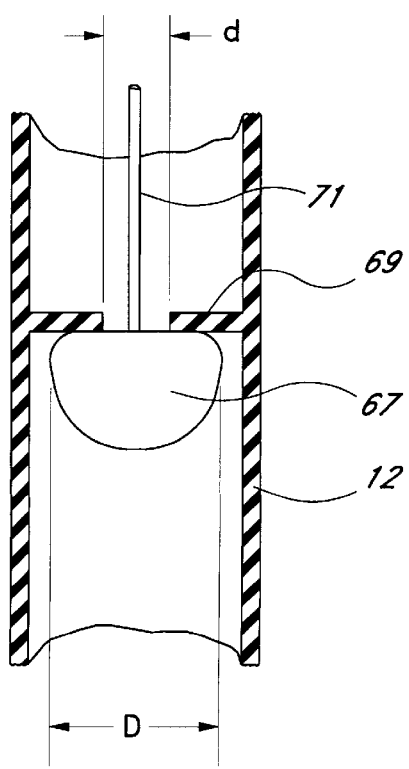
FIG. 54 is an alternate embodiment of the valve illustrated in FIGS. 52 and 53.

FIG. 54 illustrates an alternative embodiment of the tethered ball type valve. In accordance with this embodiment, when the valve is in the closed position the area of fluid in contact with the ball portion 67 of the valve has a diameter "d" which is less than the diameter "D" of the ball portion 67 of the valve. Because the area of fluid in contact with the ball portion 67 of the valve in the closed position is less than the area of fluid in contact with the ball portion 67 of the valve when the valve is in the open position, the pressure required to open the valve is more than the pressure required to keep the valve in the open position. Thus, little resistance to flow is encountered after the opening pressure is achieved.

As will be apparent to one of ordinary skill in the art, a variety of structures other than the valves described above could be used to accomplish the function of the valve 24. For instance, the valve 24 could comprise a trap door type valve with an integral elastomeric return spring hinge or tether. Such a valve preferably has a relatively high opening pressure, such as from about 5–80 cmH$_2$O, and more preferably from about 5–20 cmH$_2$O, above which little resistance to flow is encountered. A multi-leaflet valve having struts to control baseline pressure or a poppet type valve having an integral elastomeric spring could also be used to accomplish the function of valve 24.

For convenience, the valves described above were discussed with reference to valve assembly 10. One of ordinary skill in the art will recognize, however, that the valves described above can also be used with other embodiments of the present invention described in the subject application.

The opening pressure of the valve 24 depends on the type of valve chosen and the etiology of the patient's incontinence. The opening pressure of the valve, prior to being positioned within the patient, ranges from approximately 2–100 cmH$_2$O, more preferably from approximately 5–20 cmH$_2$O, and most preferably from approximately 5–10 cmH$_2$O. As discussed below, however, after the valve is properly positioned within the patient, the opening pressure of the valve varies in response to physiologic parameters.

Referring to FIG. 5, an elevational cross-sectional view of the valve assembly is shown positioned relative to the bladder 30 and the urethra 40. The urethra 40 is diagrammatically divided into a proximal portion 48 and a distal portion 50. An internal urethral sphincter 44 and an external urethral sphincter 46 are also schematically shown. As illustrated in FIG. 5, the distal end 20 of tubular body 12 is located within the proximal portion 48 of the urethra 40 between the internal urethral sphincter 44 and the external urethral sphincter 46. Preferably, the valve 24 is also located in the proximal portion 48 of the urethra, although it can alternatively be positioned elsewhere along the flow path between the bladder 30 and the distal end 20 of the valve assembly 10. Optionally, a radiopaque material, such as gold, tantalum, or barium sulfate can be incorporated into the valve to ensure proper positioning. Preferably, the radiopaque material is incorporated as a visualization ring into the distal end 20 of the tubular body 12.

Although knowledge of the physiology of the bladder and the urethra is incomplete, the external urethral sphincter is believed to be located approximately 1.0 to 4.0 cm, and more typically approximately 1.5 to 2.5 cm, distal to the bladder neck 42 in women, and approximately 5.0 to 6.0 cm distal to the bladder neck 42 in men. The external urethral sphincter is believed to primarily be responsible for the urethral pressure profile illustrated in FIG. 6. As can be seen in FIG. 6, urethral pressure is highest approximately 2 cm distal to the bladder neck. The inventors believe that in some instances the top portions of the curves illustrated in FIG. 6 may extend over a larger range of urethral length. In order to fully take advantage of the urethral pressure gradient, the valve 24 and the tubular body 12 preferably do not extend distal to the external urethral sphincter. More preferably, the tubular body 12 extends less than or equal to about 2.0 cm distal to the bladder neck. The relatively short length of the tubular body 12 allows the valve to be maximally exposed to the urethral pressure gradient, thereby aiding in keeping the valve 24 closed while the bladder is filling. During micturition, however, the urethra relaxes, removing this back pressure or closing pressure and aiding in the voiding process.

The urethral pressure gradient described above, also aids the valve assembly 10 in maintaining urinary continence during changes in physiologic parameters, such as increases in abdominal pressure caused by coughing. This aspect of the present invention is illustrated diagrammatically in FIGS. 7A and 7B. In FIGS. 7A and 7B, "a" equals resting intra-abdominal pressure, "b" equals resting bladder pressure, "u" equals resting urethral pressure, and "A" equals abdominal pressure rise on coughing. As can be seen in FIG. 7B, an increase in abdominal pressure increases both the bladder pressure and the urethral pressure. Because of the relatively short tubular body 12 of the present invention, however, the increase in urethral pressure caused by the increase in abdominal pressure is transmitted to the distal side of the valve 24, thereby momentarily increasing the effective opening pressure of the valve to help maintain valve closure during the increase in abdominal pressure.

In addition to the urethral pressure gradient described above, the bladder neck and the urethra also exert an inwardly directed force, which can enhance the function of the valve assembly 10 of the present invention. For instance, during bladder filling, the urethra exerts inwardly directed forces on the tubular body 12 and the valve 24, which help to keep the valve closed during the filling phase.

Conversely, during micturition, the pressure exerted by the bladder neck and the urethra decreases, thereby decreasing the radial or compressive force exerted on the tubular body and the valve. This decrease in radial or compressive force lowers the opening pressure of the valve and thus facilitates opening of the valve during micturition. Thus, although any of a variety of valve structures can be utilized in the valve assembly 10, valve structures which exhibit an increased opening pressure in response to inward compressive forces or radially inward compression are often preferred.

In contrast to the relatively short valve assembly 10 of the present invention, prosthetic urethral valve devices that extend into the meatus and/or have portions of the device external to the body are unable to take advantage of the urethral pressure gradient and radial forces described above.

Another advantage of the relatively short length of the valve assembly of the present invention is that it minimizes the risk of infection. In contrast, prosthetic urethral valve devices that extend into the meatus and/or have portions of the device external to the body provide a direct path for bacteria and other microorganisms to enter the urinary tract.

Figure 8:
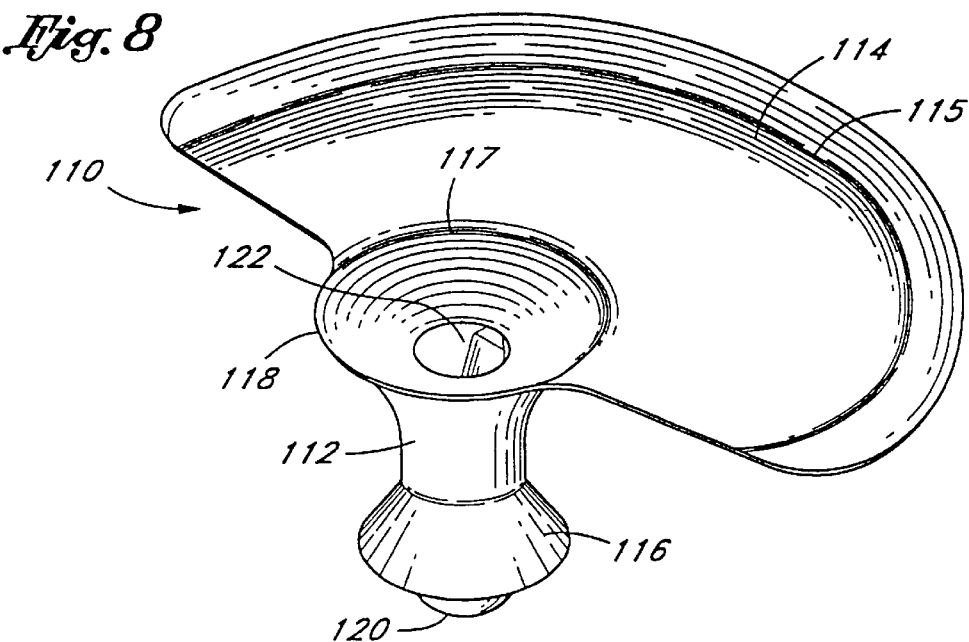
FIG. 8 is a perspective view of an alternate embodiment of the prosthetic urethral valve according to the present invention.

Referring to FIGS. 8–15, there is shown an alternate embodiment of the valve assembly of the present invention. As illustrated in FIG. 8, the valve assembly 110 includes a tubular body 112 having a proximal end 118, a distal end 120 and a central lumen 122 extending therethrough. The valve assembly also includes a first anchor 114, a gripping boss 127, and reinforcing rings 115, 117.

In addition to the first anchor 114, preferably the valve assembly 110 also includes a second anchor 116. The illustrated second anchor 116 is an annular flange attached to the tubular body 112 at a point between the proximal end 118 and the distal end 120 of the tubular body. As illustrated in FIG. 8, the second anchor of the alternate embodiment preferably inclines distally from tubular body 112, thereby providing a mechanical bias against distal dislodgement of the valve assembly from the patent.

Figure 9:
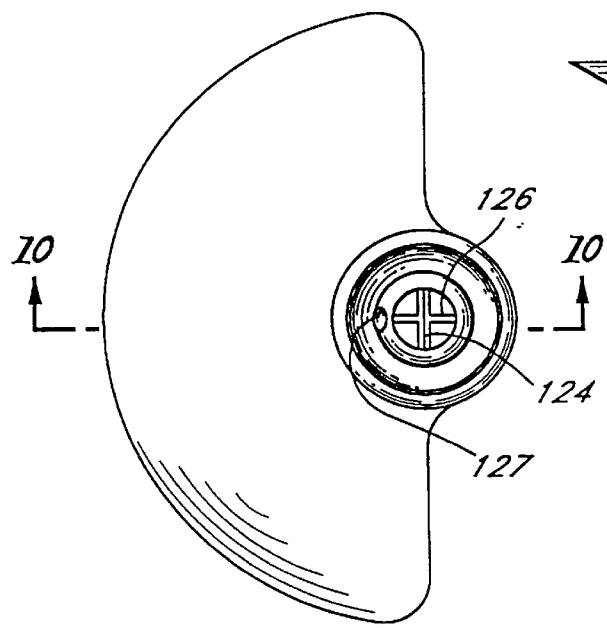
FIG. 9 is a bottom view of the valve depicted in FIG. 8.
Figure 10:
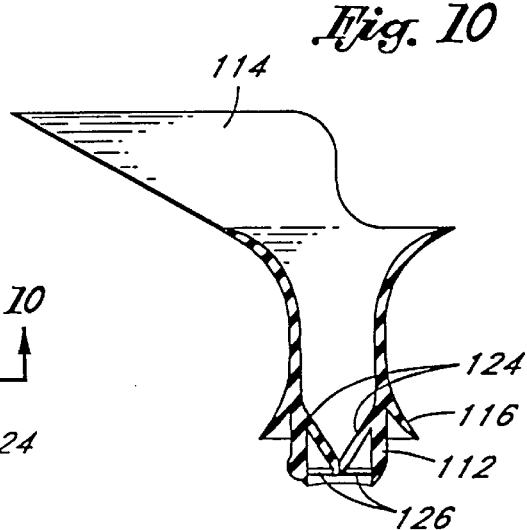
FIG. 10 is an elevational cross-sectional view taken along line 10—10 of FIG. 9.
Figure 11:
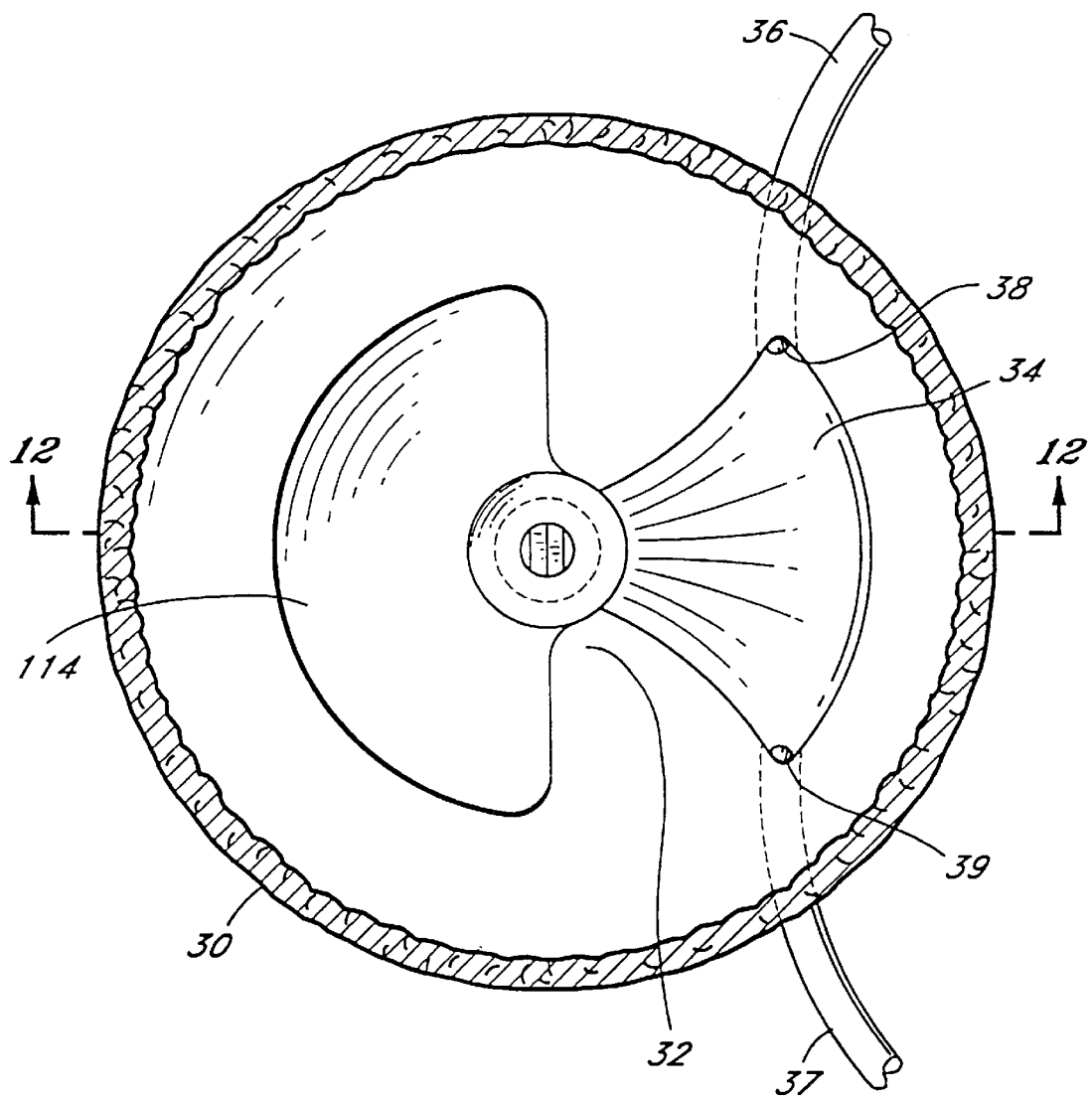
FIG. 11 is a transverse cross-sectional view through the bladder showing a top view of the alternate embodiment of the device positioned in the bladder.

The valve assembly 110 also includes a valve 124, such as a duckbill valve, which is preferably located within the lumen 122 of tubular body 112 between the proximal end 118 and the distal end 120 of the tubular body. As illustrated in FIG. 9, the orientation of valve 124 is preferably rotated approximately 90° relative to the valve depicted in FIG. 2. Thus, the coaptive edges of the two duckbill leaflets extend side to side when the valve is properly positioned in the patient. In addition, as illustrated in FIG. 10, optional valve supports 126 can be included to increase the opening pressure of the valve, if necessary, based on the characteristics of the material used to construct the valve assembly 110.

The length of the tubular body 112 of the valve assembly of the alternate embodiment is approximately the same as that of the valve assembly of FIGS. 1–5. As illustrated in FIG. 10, however, the distance between the valve 124 and the proximal end of the tubular body 112 of the alternate embodiment is greater than the distance between the valve 24 and the proximal end of the tubular body 12 of the valve assembly 10 illustrated in FIG. 3. Preferably the distance between the valve 124 and the proximal end of the tubular body is approximately 1.0–3.0 cm in the alternative embodiment, compared to approximately 0.5–2.0 cm in the embodiment of the valve 24 depicted in FIG. 3. The increased distance between the valve 124 and the proximal end of the tubular body in the alternate embodiment is especially useful in patients suffering from incontinence caused by hypermobility.

Figure 13:
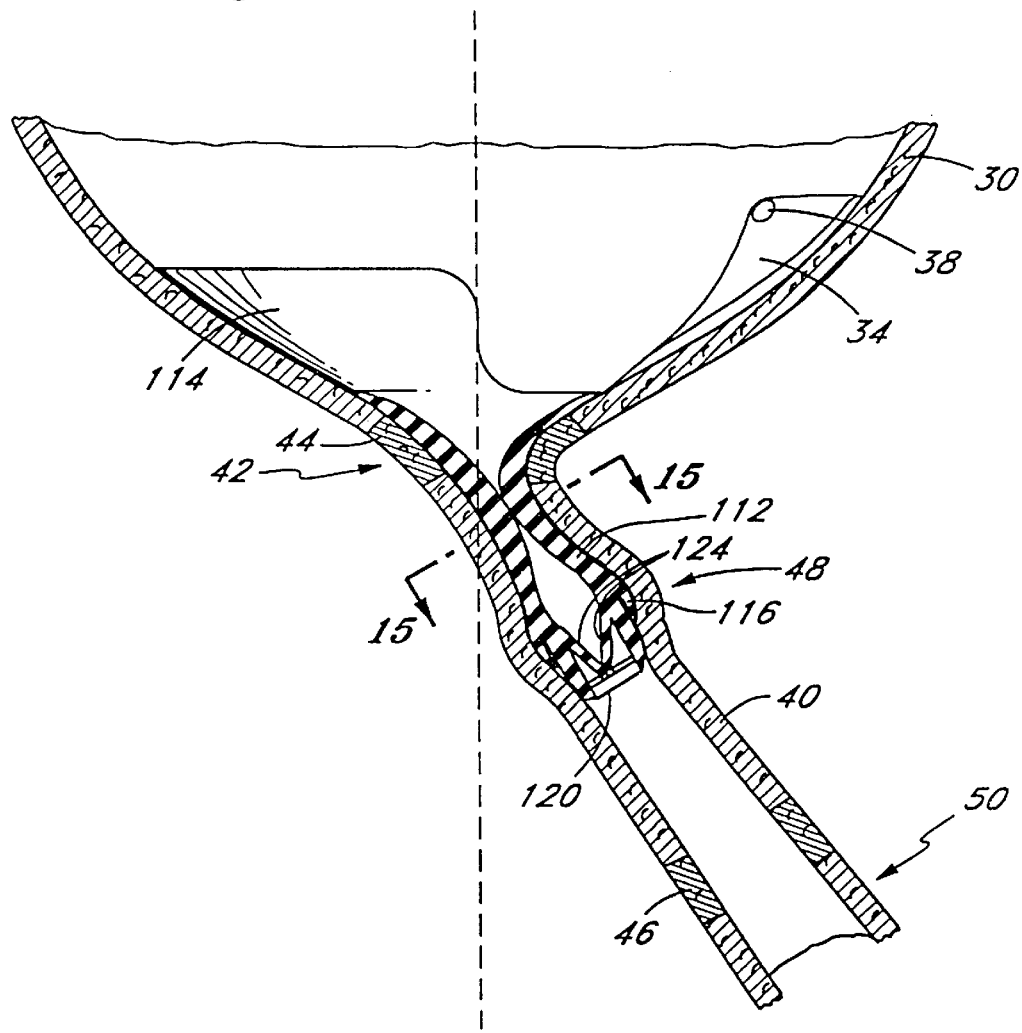
FIG. 13 illustrates the valve assembly of FIG. 12 during a hypermobility event.

In patients suffering from incontinence caused by hypermobility, the bladder neck and proximal urethra rotate and descend in response to increases in intraabdominal pressure. During a hypermobility event, the orientation of the urethra relative to the bladder may change between approximately 20° and 90°. In such patients, rotation and descent of the bladder neck and urethra result in an uneven transmission of intra-abdominal pressure to the bladder and urethra. This can cause the bladder pressure to exceed the urethral pressure by as much as 100 cmH$_2$O, resulting in incontinence. As illustrated in FIG. 13, however, the increased distance between the valve 124 and the proximal end of the tubular body 112 of the alternate embodiment allows the tubular body to kink during a hypermobility event, thereby occluding the lumen of the tubular body, which helps prevent undesired leakage of urine through the valve assembly.

Figure 12:
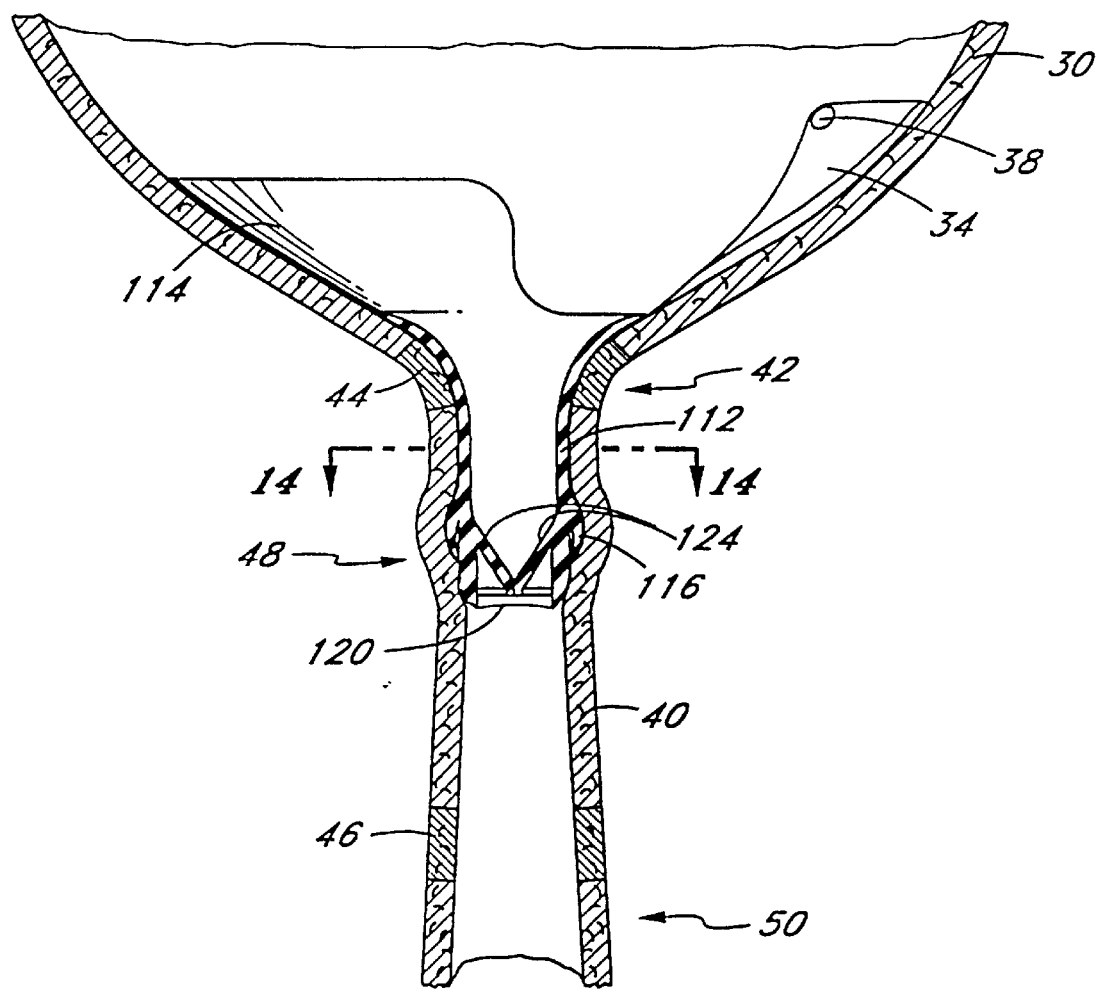
FIG. 12 is an elevational cross-sectional view taken along line 12—12 of FIG. 11.

FIGS. 12 and 13 illustrate the kinking feature of the tubular body 112 of the alternate embodiment of the present invention. FIG. 12 is an elevational cross-sectional view of the valve assembly positioned in the patient prior to a hypermobility event. In contrast, FIG. 13 illustrates the same view of the valve assembly during a hypermobility event. As can be seen, during the hypermobility event, the proximal portion of the tubular body 112 kinks or collapses, which helps to maintain continence without having to unduly increase the opening pressure of the valve 124.

Figure 14:
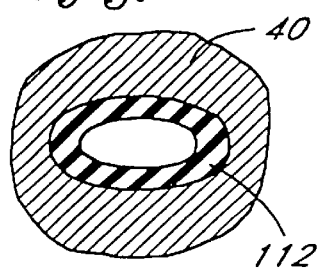
FIG. 14 is a cross-sectional view taken along line 14—14 of FIG. 12.
Figure 15:
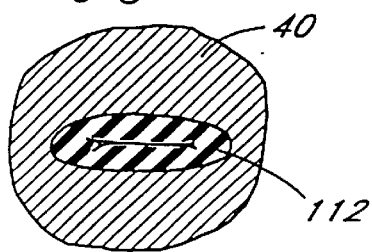
FIG. 15 is a cross-sectional view taken along line 15—15 of FIG. 13.

In order to facilitate kinking of the tubular body 112, the tubular body preferably has a thinner wall and/or a non-circular cross section, such as elliptical or oval, at the desired point of kinking. In many patients, such as those suffering from incontinence caused by hypermobility, the desired point of kinking would be in the proximal portion of the tubular body approximately 0.1–1.5 cm distal to the proximal end 118 of the tubular body. In some patients, however, the desired point of kinking may be located elsewhere along the tubular body 112 as will be evident to one of skill in the art. In addition, the device of the present invention may have a thinner wall and/or non-circular cross section throughout the length of the tubular body. A tubular body having a non-circular cross section is illustrated in FIGS. 14 and 15, which show the lumen of the tubular body before and kinking of the tubular body caused by a hypermobility event.

As discussed earlier in connection with the valve assembly of FIGS. 1–5, one of ordinary skill in the art will recognize that a variety of structures other than the first anchor 114, second anchor 116, and valve 124 illustrated in FIGS. 8–13 could be used in accordance with the alternate embodiment of the present invention.

The valve assembly of the present invention can be manufactured using any of the variety of means known to those of ordinary skill in the art. Preferably the valve is injection molded into an integral unit. Alternatively, the valve assembly 10, 110 can be fabricated from two or more separately molded units, which are secured using conventional techniques such as thermal bonding, solvent bonding or suitable adhesives known in the art. For instance, the valve 24, 124 and the remainder of the valve assembly 10, 110 could be manufactured separately and then combined into a single unit using conventional methods known to those of ordinary skill in the art.

The device of the present invention may be made of any suitable resilient material which is biocompatible and resistant to a urine environment. Preferred materials include silicone rubbers, latex rubbers and polyurethane, with silicone rubbers being the most preferred. In addition to facilitating functioning of the device, the choice of soft, resilient materials also enhances patient comfort.

To minimize encrustation and infection, coatings well known to those of ordinary skill in the art, such as silver flouropolymers or sulfated polysaccharide pentosanpolysulfate, can be applied to the device.

The dimensions and configuration of the valve assembly 10, 110 can be varied considerably to suit particular design criteria desired for a particular application and still embody the present invention. Dimensions are largely limited by anatomical considerations as discussed above with respect to the length of the tubular body 12, 112, which is preferably approximately 0.5 cm to 3 cm in length, and more preferably less than about 1.5 cm in length. The diameters of the tubular body 12, 112 and second anchor 16, 116 are also dictated by anatomical considerations. In particular, the diameters of the tubular body and second anchor are chosen to fit securely within the urethra yet not exert an excess outward force on the urethra so that the tubular body can be compressed in response to urethral forces. Typical ranges for the outside diameter of the tubular body are approximately 0.5 cm to 0.8 cm (15–24 French), preferably about 0.6 cm (18 French). Typical ranges for the outside diameter of the second anchor are approximately 0.66 cm to 1 cm (20–30 French), preferably about 0.08 cm (24 French). The wall thickness of the tubular body is generally within the range of from about 0.15–3 mm, preferably about 0.25–1 mm, and more preferably about 0.4 or 0.5 mm.

In addition to anatomical considerations, the size and shape of various components of the valve assembly 10, 110 are also governed by the type of material used to construct the valve assembly.

A nonsurgical procedure for maintaining urinary continence in a patient, is generally accomplished as follows. A prosthetic urethral valve assembly such as 10 or 110 of the present invention is selected by the physician based on the sex of the patient as well as other anatomical and medical considerations. Using an installation device, such as the cystoscope 221 and grasping forceps 225 illustrated in FIG. 16 and described below, the physician transurethrally positions the prosthetic urethral valve assembly so that both the valve 24, 124 and the distal end 20, 120 of the tubular body 12, 112 lie between the internal urethral sphincter and the external urethral sphincter so that the opening pressure of the valve varies in response to changes in physiologic parameters.

Figure 16:
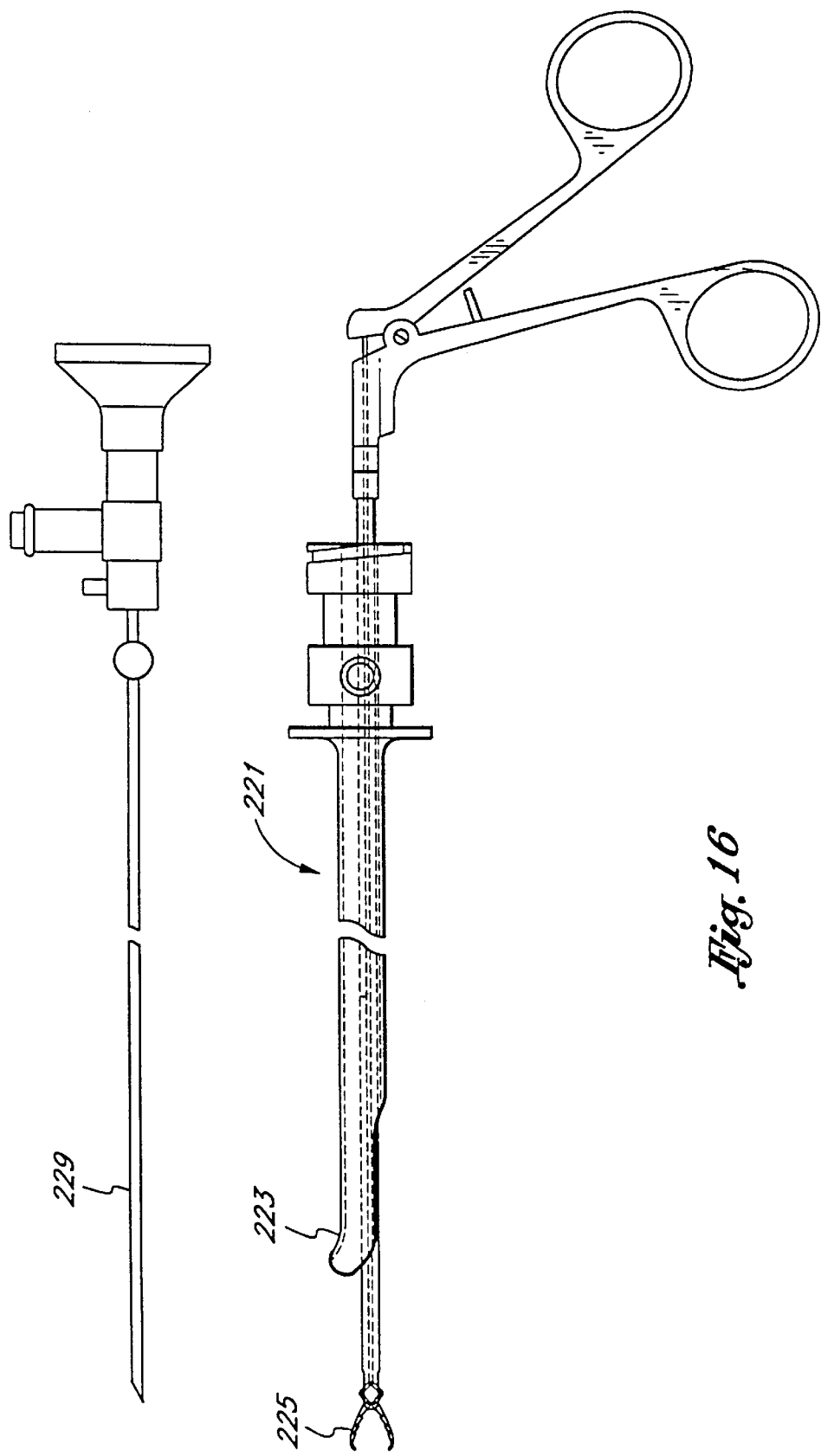
FIG. 16 is a partially exploded side view of various components of a device for installing the prosthetic urethral valve of the present invention.

With reference to the installation device depicted in FIG. 16, one method of positioning the valve assembly 10, 110 is accomplished as follows. The physician transurethrally advances the cystoscope 221 and rod lens 229 into the bladder in accordance with conventional techniques. The physician then performs a standard cystoscopic examination of the bladder and fills the bladder with an irrigant. After performing the cystoscopic examination, the physician removes the cystoscope 221 from the urethra and removes the rod lens 229 from the cystoscope. The grasping forceps 225 are then passed through the cystoscope 221 so that the forceps 225 extend beyond the distal end 223 of the cystoscope 221 as illustrated in FIG. 16. A water soluble lubricant, such as K-Y jelly is applied to the outside of the valve assembly. The forceps 225 are used to releasably engage the valve assembly. For example, as illustrated in FIG. 17, the gripping boss 127 of the valve assembly is preferably releasably engaged by the forceps 225. The physician then carefully pushes the valve assembly into the distal end 223 of the cystoscope 221, collapsing the valve assembly as needed. The physician may also gently withdraw the forceps proximally to pull the valve assembly into the distal end of the cystoscope.

After placing the valve assembly 10, 110 into the distal end of the cystoscope, the physician passes the cystoscope through the urethra and into the bladder. Rod lens 229 is then inserted into the cystoscope 221 until it contacts the valve assembly. Using the rod lens and the forceps 225, the physician axially displaces the valve assembly distally out of the distal end 223 of the cystoscope 221 and into the bladder. While viewing the valve assembly 10, 110 in the bladder using the rod lens 229, the physician can rotate the forceps, if necessary, to properly orient the valve assembly and the first anchor 14, 114 relative to the base of the bladder and the trigone region.

While keeping the forceps stationary relative to the cystoscope, the physician withdraws the cystoscope, proximally thereby placing traction on the valve assembly in order to lodge the first anchor relative to the base of the bladder while avoiding contact between the first anchor and trigone region. Optionally, the position of the valve assembly can be confirmed using well known radiologic methods, such as in those embodiments in which a visualization ring has been incorporated into the valve assembly.

If the valve assembly is not properly positioned, the physician can readvance the cystoscope and the valve assembly into the bladder to rotate and reposition the valve. After the valve assembly is properly positioned, the physician releases the valve assembly from the forceps and withdraws the cystoscope, including the forceps and rod lens, from the patient.

The valve assembly 10, 110 can also be positioned using a standard embolectomy balloon catheter rather than the grasping forceps 225 described above. After performing a standard cystoscopic examination of the bladder and filling the bladder with an irrigant, the physician removes the cystoscope 221 from the urethra and removes the rod lens from the cystoscope leaving the bridge attached. The balloon catheter is then passed through the bridge and the cystoscope 221 so that the inflatable portion of the balloon catheter extends beyond the distal end 223 of the cystoscope. A water soluble lubricant, such as K-Y jelly, is applied to the outside of the valve assembly 10, 110. A standard balloon catheter threading tube is then advanced through the tubular body 12, 112 from the proximal end 18, 118 to the distal end 20, 120 of the tubular body.

The tip of the balloon catheter is then placed against the threading tube and the physician gradually extends both the balloon catheter and threading tube through the valve 24, 124 of the valve assembly 10, 110. The physician then carefully pushes the valve assembly into the distal end 223 of the cystoscope 221, collapsing the valve assembly as needed. After placing the valve assembly into the distal end of the cystoscope, the physician passes the cystoscope through the urethra and into the bladder.

The balloon catheter is then advanced distally so that the inflatable portion of the balloon catheter extends beyond the distal end of the cystoscope. The balloon is then inflated by the physician using conventional inflation media, such as fluid. The rod lens 229 is then inserted into the cystoscope 221 until it contacts the valve assembly. Using the rod lens (or other push rod structure), the physician axially displaces the valve assembly distally beyond the distal end of the cystoscope and into the bladder where it remains coaxially positioned about the balloon catheter shaft proximally of the balloon.

While viewing the valve assembly in the bladder using the rod lens, the physician can rotate the shaft of the balloon catheter, if necessary, to properly rotationally orient the valve assembly and the first anchor 14, 114 relative to the base of the bladder and the trigone region. During or after retraction of the cystoscope through the bladder neck, the physician retracts the inflated balloon catheter proximally in order to lodge the first anchor 14, 114 relative to the base of the bladder while avoiding contact between the first anchor and the trigone region. Optionally, the axial position of the valve assembly can be confirmed using well known radiologic methods, such as in those embodiments in which a visualization ring has been incorporated into the valve assembly. If the valve assembly is not properly positioned, the physician can readvance the cystoscope, balloon catheter, and valve assembly into the bladder to reposition the valve. After the valve assembly is properly positioned, the physician deflates the balloon catheter and withdraws the cystoscope, including the deflated balloon catheter and rod lens, from the patient.

Upon positioning internally as described above, the valve assembly 10 is automatically activated in response to physiologic conditions and thus can be controlled voluntarily by the patient without manual intervention.

As needed, the valve assembly 10, 110 can be removed from the patient and replaced with a new valve assembly. Removal of the valve assembly can be accomplished in a variety of ways, including through use of the cystoscope 221, rod lens 229, grasping forceps 225 and/or embolectomy balloon catheter described above. For example, the grasping forceps 225 are used to grasp the tab 27. The valve assembly can then be drawn into the distal end of a tubular structure such as a channel in the cystoscope 221. Preferably, the valve is drawn into the cystoscope while the cystoscope is simultaneously advanced in the distal direction to avoid pulling the first anchor through the bladder neck.

Alternatively, the valve assembly can be pushed distally from its installed position into the bladder, using the grasping forceps 225, rod lens 229 or other pushing structure. Preferably the physician will keep a grasp on the valve assembly such as by tab 27 using forceps 225 throughout the proximal displacement step. Once the valve assembly is in the bladder, it can be pulled into the end of the cystoscope. With certain anchor designs, the anchor may simply be pulled transurethrally from the patient.

For convenience, the methods of positioning and removal described above were discussed with reference to valve assembly 10, 110. One of ordinary skill in the art will recognize, however, that the methods of positioning and removal described above can also be used with other embodiments of the present invention described in the subject application.

Referring to FIGS. 18–20, there is shown an alternate embodiment of the present invention. The device 210 includes a tubular body 212 having a proximal end 218, a distal end 220 and a central lumen 222 extending therethrough. The device 210 also includes a first anchor 214, a gripping boss 227 and reinforcing rings 215, 217.

In addition to the first anchor 214, the device 210 may also include a second anchor 216. The structure and function of the second anchor 216 illustrated in FIGS. 18–20 is generally similar to that of the previously described embodiments of the present invention.

The device 210 preferably does not include a discrete valve. One of ordinary skill in the art will recognize, however, that the device 210 could include a discrete valve, such as those previously described in the subject application.

The device 210 functions primarily as a bulking agent or sealing device, which reversibly seals by collapsing at least part of the tubular body in response to the previously described inwardly directed urethral forces. These forces on the urethra help to cause the tubular body to collapse and seal when micturition is undesired, thereby maintaining urinary continence. Conversely, when micturition is desired, the pressure exerted by the urethra and bladder neck decreases, thereby allowing the tubular body to open.

The tubular body 212 of the device 210 can also function as a reversible seal by kinking due to for instance bending of the tubular body in response to the previously described rotational descent of the bladder neck and urethra, such as during a hypermobility event.

The dimensions and configuration of the device 210 are generally similar to those of the previously described embodiment illustrated in FIGS. 8–15. The tubular body 212 may be longer and have a thicker wall, however, in order to enhance the device's ability to serve as a bulking agent, yet still take advantage of the urethral pressure gradient and other previously discussed aspects of urinary anatomy/physiology.

Typical ranges for the length of the tubular body portion 212 of the device 210 are approximately 1.0–3.0 cm, preferably about 1.0–2.0 cm. Typical ranges for the outside diameter of the tubular body 212 and second anchor 216 are generally similar to those of the previously described embodiments of the present invention. Typical ranges for the wall thickness of the tubular body 212 of the device 210 are approximately 0.15–3 mm, preferably about 0.2 or 0.4–1.5 mm, and more preferably about 0.4 or 0.5 mm. The tubular body 212 of the device 210 can also have a variable thickness wall as previously discussed, wherein the wall of the proximal portion of the tubular body is thinner than that of the distal portion to facilitate kinking of the proximal portion, such as a during a hypermobility event. In addition, as previously discussed, in order to facilitate kinking, the tubular body can have a non-circular cross section, such as elliptical or oval, at the desired point of kinking or throughout the length of the tubular body.

As will be apparent to one of skill in the art, the device 210 can be manufactured in accordance with any of a variety of techniques and materials, such as those previously described. Also as discussed above, in addition to anatomical considerations, the size and shape of various components of the device 210 are governed by the type of material used to construct the device. For instance, particularly compliant materials, such as the silicone rubbers and other materials described above, facilitate urethral compression and/or kinking of the tubular body of the device, especially in devices having a thicker walled tubular body.

As with the previously described embodiments of the present invention, one of ordinary skill in the art will recognize that a variety of structures other than the first anchor 214 and second anchor 216 could be used in accordance with the device 210. One of ordinary skill in the art will also recognize that any of a variety of installation and removal techniques, including those described in the subject application, could be used to position the device 210 within the urinary tract of the patient and/or to remove the device therefrom.

Referring to FIGS. 21–25 and 27, there is shown an alternative embodiment of the present invention. The device 310 includes a tubular body 312 having a proximal end 318, a distal end 320 and a central lumen 322 extending therethrough.

As illustrated in FIG. 67, a tether 357 may be attached at the distal end 320 of the tubular body 312 to facilitate transurethral placement of the device. As will be apparent to one of skill in the art, a tether may also be used with the other embodiments of the invention described in the subject application.

Preferably, the tether 357 is a removable suture so that after the device has been positioned, the suture can be removed to decrease the risk of infection. The tether 357 may also comprise a non-removable suture or be an extension of the tubular body itself. If the tether 357 is a non-removable suture or extension of the tubular body, care should be taken to ensure that the tether does not extend beyond the urethral meatus in order to minimize the risk of infection. In those cases in which a non-removable tether is used, the tether 357 may also be used to facilitate removal of the device.

Alternatively, the tubular body 312 may include a gripping tab or boss similar to that of the previously described embodiments of the present invention in order to facilitate transurethral placement and removal of the device.

The device 310 also includes a first anchor 314. The first anchor 314 preferably has an increasing diameter in the proximal direction and conforms to the bladder neck and/or proximal urethra. The outer diameter of the first anchor 314 at its proximal end 331 is preferably approximately 0.5–2.0 cm, more preferably about 0.8–1.3 cm.

The first anchor 314 functions to releasably secure the device 310 relative to the bladder neck and urethra. The first anchor 314 also helps prevent urine from escaping around the exterior of the device. When positioned intraurethrally, as illustrated in FIG. 66, the first anchor also serves a bulking/sealing function as discussed more fully below.

The first anchor is preferably an atraumatic retention structure which is enlargeable from a first, collapsed configuration for transurethral placement to a second, enlarged configuration for anchoring the device 310 relative to the bladder neck and/or urethra. In the embodiment illustrated in FIGS. 21–25 and 27, the first anchor 314 comprises a pliable generally circular retention structure that inclines generally radially outwardly in the proximal direction from the proximal end 318 of the tubular body 312 as illustrated in FIGS. 21, 23 and 25. The retention structure is mechanically biased in the direction of the second, enlarged configuration as illustrated to help prevent the device 310 from being displaced after positioning of the device in the patient as well as to help prevent urine from escaping around the exterior of the device.

Although shown as radiused in FIGS. 21 and 23, the first anchor 314 of the device 310 can also extend outwardly in a conical shape in the proximal direction from the proximal end 318 of the tubular body 312 as illustrated in an alternate preferred embodiment of the present invention depicted in FIG. 23A. The outer diameter of the conical-shaped first anchor 314 at its proximal end 331 is preferably approximately 0.5–2.0 cm, more preferably about 0.8–1.3 cm.

Figure 33:
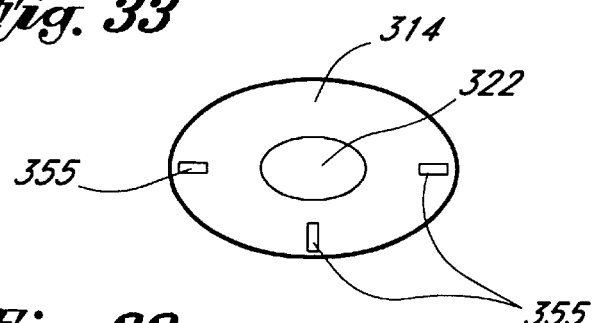
FIG. 33 is a top view of the embodiment depicted in FIG. 32.
Figure 32:
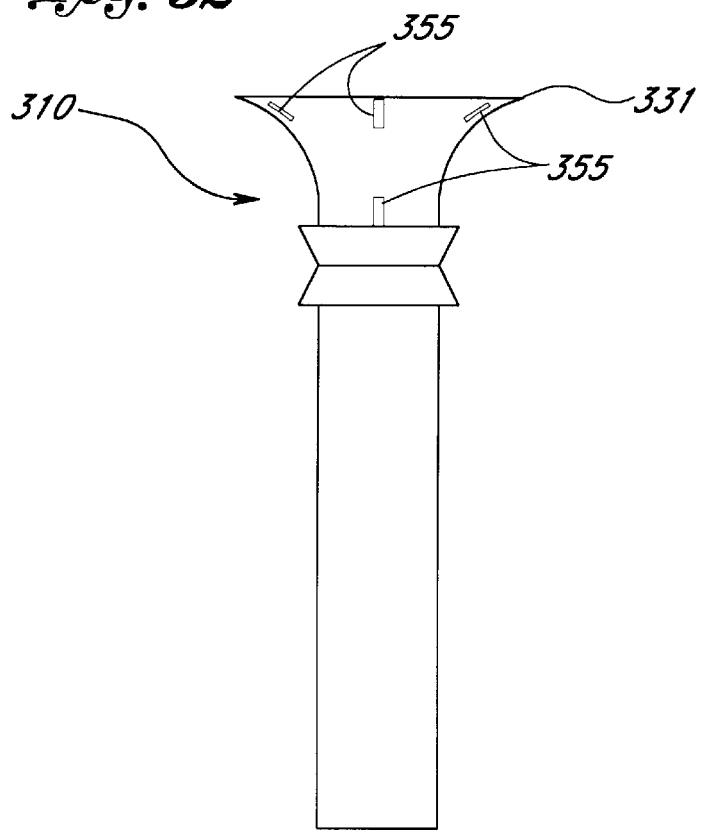
FIG. 32 is an elevational side view of an alternate embodiment of the device according to the present invention.
Figure 34:
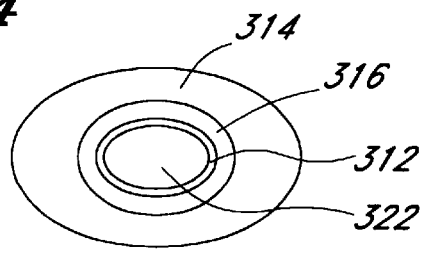
FIG. 34 is a bottom view of the embodiment depicted in FIG. 32.
Figure 44:
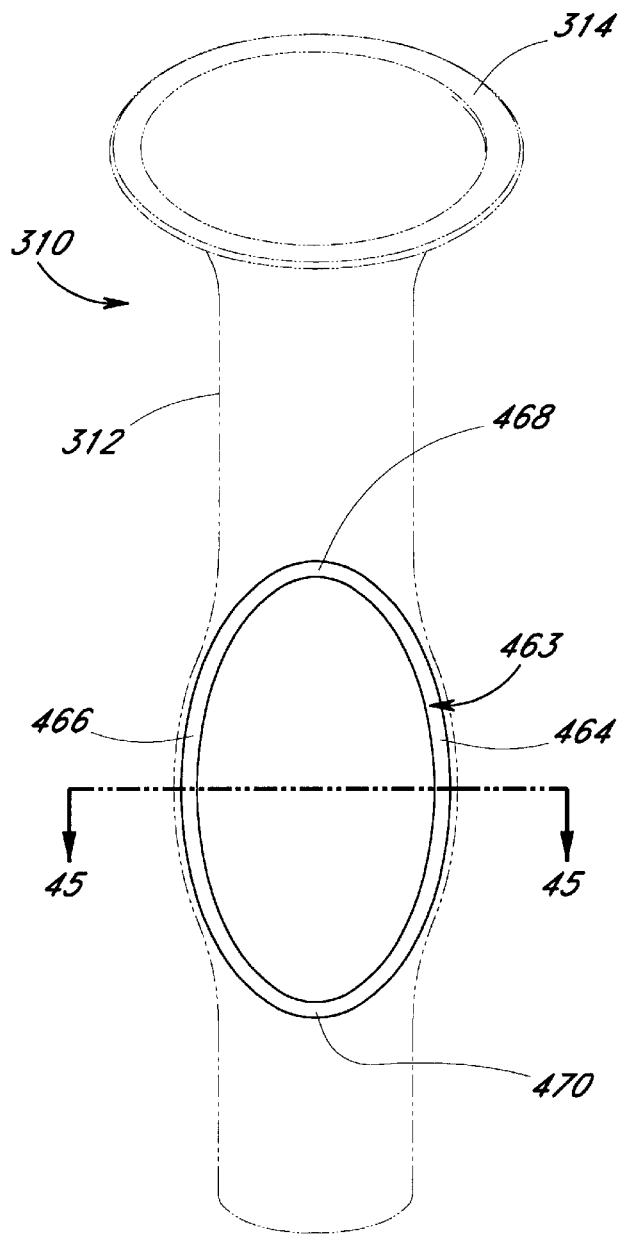
FIG. 44 is a frontal perspective view of an alternate embodiment of the device illustrated in FIG. 41.
Figure 45:
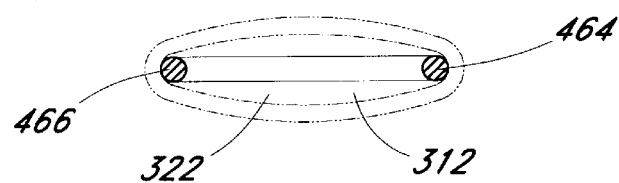
FIG. 45 is a cross-sectional view taken along line 45—45 of FIG. 44.

The first anchor 314 can also be formed in a variety of other shapes, including the oval-shaped first anchor 314 illustrated in FIGS. 32–34 and the star-shaped first anchor 314 illustrated in FIGS. 35–38. The dimensions of the oval-shaped first anchor 314 at its proximal end 331 are preferably approximately 0.3 cm along the short axis by 1.0 cm along the long axis, more preferably approximately 0.4 cm along the short axis by 0.7 cm along the long axis.

With regard to the star-shaped first anchor 314 illustrated in FIGS. 35–38, the diameter of a circle drawn through the outer points 356 of the star-shaped first anchor 314 at its proximal end 331 is preferably approximately 0.5–2.0 cm, more preferably about 0.8–1.3 cm. The diameter of a circle drawn through the inner points 359 of the star-shaped first anchor 314 at its proximal end 331 is preferably approximately 0.3–1.8 cm, more preferably about 0.6–1.1 cm.

In addition to the first anchor 314, the device 310 optionally may include a second anchor 316 to further releasably secure the device 310 and stabilize the tubular body 312 within the urethra. In the embodiment of the device illustrated in FIGS. 21–25 and 27, the second anchor is a dual annular flange that extends radially outwardly in both the proximal and distal directions. The distance between the most proximal and most distal portions of the second anchor 316 measured along the longitudinal axis of the tubular body 312 can vary, but is preferably approximately 0.2–0.8 cm, more preferably about 0.4 cm. Optionally, one or more nitinol rings can be molded into the annular flange as previously discussed.

In the illustrated embodiment, the second anchor 316 is located along the length of the tubular body between the first anchor 314 and the distal end 320 of the tubular body 312. In such cases, the location of the second anchor 316 can vary, but preferably the midpoint of the second anchor 316 measured along the longitudinal axis of the tubular body 312 is approximately 0.2–0.8 cm from the proximal end 318 of the tubular body 312, and more preferably about 0.40 cm from the proximal end 318 of the tubular body 312. In addition, the distance between the most proximal portion of the second anchor 316 and the proximal end 331 of the first anchor 314 is preferably approximately 0.4–1.2 cm, more preferably about 0.8 cm.

Alternatively, the second anchor 316 may extend distally from the distal end 320 of the tubular body 312 as illustrated in FIG. 26. The structure and location of the second anchor 316 can also be generally similar to that of the previously described embodiments of the present invention.

The devices of the present invention, such as the device 310 may also include radiopaque markers 355 such as those illustrated in FIGS. 21–23, 25–26 and 32–33 to ensure proper positioning of the device, including rotational orientation. In the illustrated embodiments, the device has three markers 355 on the first anchor 314 and one marker 355 at the proximal end 318 of the tubular body 312. The preferred radial orientation of the markers 355 is shown in FIGS. 21–23, 25–26 and 32–33. One of skill in the art will recognize that any of a number of types of radiopaque markers 355, such as gold, tantalum or barium sulfate, and radial orientations may be used to ensure proper positioning of the device 310. In addition, the markers 355 can be included in portions of the device 310 other than the first anchor 314 and proximal end 318 of the tubular body 312. As will be apparent to one of ordinary skill in the art, the markers 355 can be incorporated into the device 310 or attached to the device 310 in a number of ways. The markers 355 are preferably bonded to the device 310 using silicone, such as room temperature vulcanizing silicone (NuSil MED 2000).

The device 310 preferably does not include a discrete valve. One of skill in the art will recognize, however, that the device 310 could include a discrete valve, such as those previously described in the subject application.

As discussed above with regard to the embodiment of FIGS. 18–20, the device 310 functions preferably as an intraurethral bulking agent, which reversibly seals in response to the previously described inwardly directed urethral forces. These forces on the urethra help to collapse and seal the tubular body 312 and/or first anchor 314 when micturition is undesired, thereby maintaining urinary continence by augmenting natural urethral sealing. Conversely, when micturition is desired, the pressure exerted by the urethra and bladder neck decreases, thereby allowing the tubular body and first anchor to open. Thus, the present invention provides a dynamic device which changes in response to natural internal forces, such as physiologic and anatomic forces acting upon the urethra and/or bladder neck.

The tubular body 312 of the device 310 can also function as a reversible seal by kinking due to for instance bending in response to the previously described rotational decent of the bladder neck and urethra, such as during a hypermobility event.

A typical range for the length of the tubular body 312 of the device 310 as provided to the physician is approximately 0.5–5.0 cm. As discussed more fully below, if necessary, the tubular body 312 is cut by the physician so that the length of the device 310 is preferably approximately 0.2–1.0 cm less than the patient's measured urethral length, more preferably about 0.60 cm less than the patient's measured urethral length. Typical ranges for the outside diameter of tubular body 312 are preferably approximately 0.20–0.80 cm, more preferably 0.40–0.60 cm. Typical ranges for the outside diameter of the second anchor 316 are preferably approximately 0.50 –1.0 cm, more preferably 0.60–0.90 cm. Typical ranges for the wall thickness of the tubular body of the device 310 are approximately 0.30–0.80 mm, preferably about 0.40–0.60 mm, and more preferably about 0.50 mm.

The tubular body of the device can also have a variable thickness wall as previously discussed, wherein the proximal portion of the tubular body is thinner than that of the distal portion to facilitate kinking of the proximal portion, such as during a hypermobility event. In addition, as previously discussed, in order to facilitate kinking and sealing, the tubular body can have a non-circular cross-section, such as elliptical or oval, at the desired point of kinking or throughout the length of the tubular body.

A variety of tubular bodies having a non-circular cross-section are shown in FIGS. 28–31. The shape of the tubular body 312 optimally simulates the patient's natural urethral shape while restoring lost function without causing urinary obstruction.

FIGS. 30 and 31 illustrate an additional optional feature of the present invention. In particular, the tubular body 312 illustrated in FIGS. 30 and 31 has a stiffened posterior floor 361, which can be provided using a variety of conventional manufacturing techniques. FIG. 30 shows the tubular body in a closed position while FIG. 31 shows the tubular body in an open position. As can be seen, the shape of the stiffened posterior floor 361 remains relatively constant while the rest of the tubular body expands from the closed position to the open position during micturition. In addition, the stiffened posterior floor 361 acts as a backstop for downwardly directed abdominal pressure to help maintain continence during increases in abdominal pressure, such as during coughing.

A variety of first anchor types, second anchor types, and tubular body types have been described in the subject application in relation to specific embodiments of the present invention. One of ordinary skill in the art will recognize that these and other aspects of the present invention can also be combined in a variety of manners other than the combinations specifically described.

As will be apparent to one of skill in the art, the device 310 can be manufactured in accordance with any of a variety of techniques and materials, such as those previously described. Also as discussed above, in addition to anatomical considerations, the size and shape of various components of the device 310 are governed by the type of material used to construct the device. For instance, particularly compliant materials, such as silicone rubbers and other materials described above, facilitate urethral compression and/or kinking of the tubular body 312 of the device 310, especially in devices having a thicker walled tubular body. A preferred material for the device 310 is Dow Silicone, MDX4-4210.

As with the previously described embodiments of the present invention, one of ordinary skill in the art will recognize that a variety of structures other than the first anchor 314 and second anchor 316 could be used in accordance with the device 310. One of ordinary skill in the art will also recognize that any of a variety of installation and removal techniques, including those described in the subject application, could be used to position the device 310 within the urinary tract of the patient and/or to remove the device therefrom.

The various embodiments of the present invention, such as device 310, may also include a resilient support structure 463 as illustrated in FIGS. 39–45 to provide an additional mechanical bias to help further secure the device within the patient. The resilient support structure 463 can also be used with other tubular devices as will be apparent to one of ordinary skill in the art.

Depending on the shape of the resilient support structure 463, it can also be used to bias the tubular body 312 of the device 310 towards a flattened/closed shape as illustrated in FIGS. 41–42 and 44–45 to help maintain continence without causing urinary obstruction. In addition, the resilient support structure provides some rigidity to minimize distortion of certain portions of the device during increases in abdominal pressure.

The resilient support structure 463 can be incorporated into the device 310 as illustrated in FIGS. 39 and 40. The resilient support structure 463 can also be inserted into the lumen of the device 310 as illustrated in FIGS. 41–42 and 44–45. In the devices illustrated in FIGS. 41–42 and 44–45, the bias of the resilient support structure 463 against the tubular body 312 of the device 310 holds the resilient support structure 463 in place relative to the device 310. The resilient support structure 463 shown in FIGS. 41–42 and 44–45 can also be secured to the device 310 using conventional techniques such as thermal bonding, solvent bonding or suitable adhesive known in the art.

Figure 46:
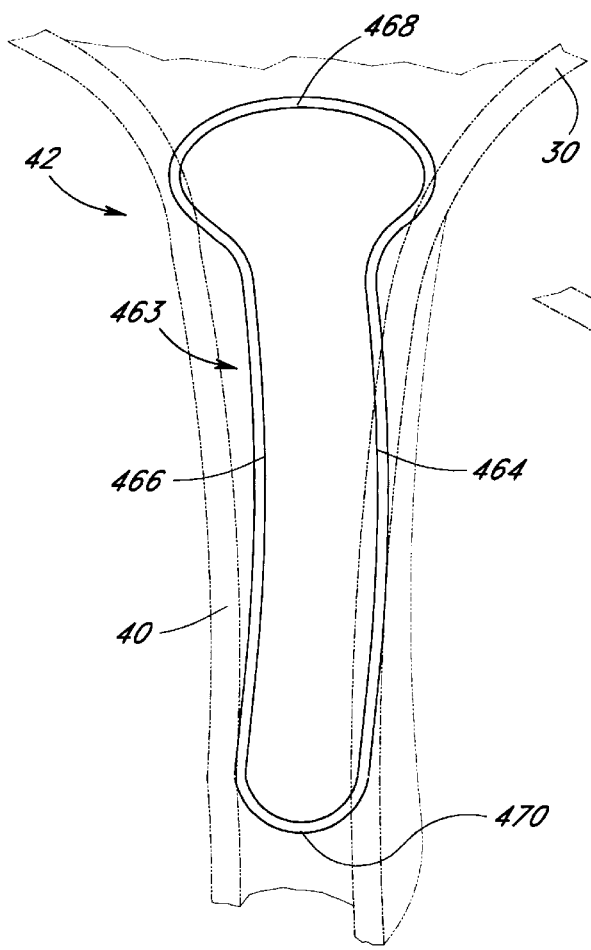
FIG. 46 is a perspective view of a resilient support structure of the present invention inserted in a urethra which is shown in phantom.
Figure 47:
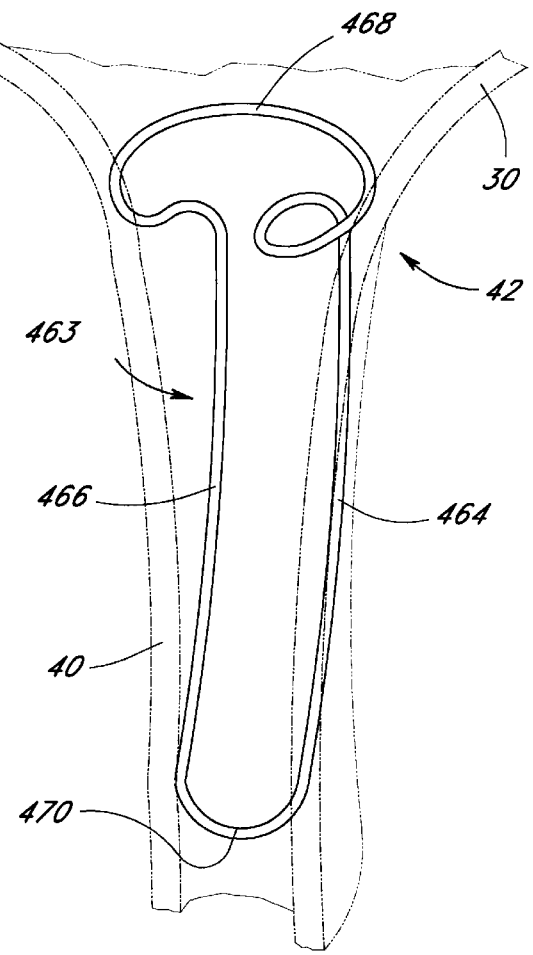
FIG. 47 is an alternate embodiment of the resilient support structure shown in FIG. 46 inserted in a urethra which is shown in phantom.
Figure 48:
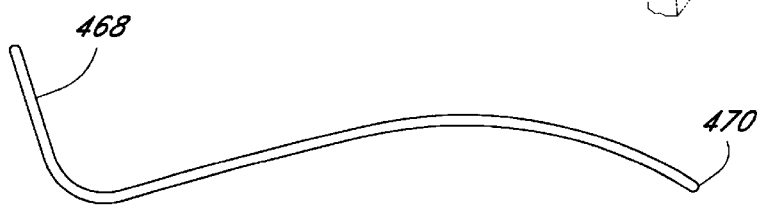
FIG. 48 is a side view of the resilient support structure shown in FIGS. 46 and 47.

The resilient support structure 463 can also be used alone as illustrated in FIGS. 46–48. In FIGS. 46 and 47, the urethra 40, bladder neck 42, and a portion of the bladder 30 are shown schematically in phantom. In the embodiment of the present invention illustrated in FIGS. 46–48, a portion of the resilient support structure 463 extends into the bladder to help secure the resilient support structure 463 within the urinary tract. In other cases, the resilient support structure 463 might be totally intraurethral or extend only from the urethra to the bladder neck as opposed to extending into the bladder. The resilient support structure 463 is preferably shaped so that it exerts a biasing force against the urethra to further secure the resilient support structure 463 within the urinary tract as well as to bias the urethra towards a flattened cross-sectional shape to help maintain continence.

The resilient support structure 463 of FIGS. 39–48 preferably comprises two axially extending segments 464 and 466 extending from a first end portion 468. The resilient support structure 463 may also include a second end portion 470. The distance separating the first axially extending segment 464 from the second axially extending segment 466 is preferably greater than the diameter of the urethra to help anchor the resilient support structure 463 therein. The first and second axially extending segments 464 and 466 may also be curved as illustrated in FIGS. 43 and 48 so that after the resilient support structure 463 is positioned in the patient, a portion of the urethra is biased in the cephalad direction.

The first end portion 468 of the resilient support structure 463 may comprise a loop of varying shapes as illustrated in FIGS. 39, 41, 46 and 47. The first end portion 468 may have a diameter which is greater than the distance separating the first axially extending segment 464 from the second axially extending segment 466 to further anchor the resilient support structure 463, especially in those embodiments of the present invention in which the first end portion 468 of the resilient support structure 463 extends into the bladder neck and/or into the bladder.

The dimensions of the resilient support structure 463 of FIGS. 39–48 are largely governed by anatomical considerations and the size/shape of the device, if any, with which it is being included. One of ordinary skill in the art will recognize that a variety of sizes and shapes other than those illustrated for the resilient support structure 463 could be used in accordance with the present invention.

The resilient support structure 463 may be made of any suitable resilient material. Preferred materials include stainless steel, nitinol, titanium, and polymeric materials, such as polyurethane and polypropylene.

One of ordinary skill in the art will recognize that any of a variety of installation and removal techniques, including those described in the subject application, could be used to position devices having a resilient support structure 463, such as the devices illustrated in FIGS. 39–45, within the urinary tract of the patient and/or to remove such devices therefrom.

One of ordinary skill in the art will also recognize that the installation and removal techniques described in the subject application can also be used to position the resilient support structure 463 of FIGS. 46–48. In such cases, however, instead of releasably engaging the distal end of a tubular body, the device of FIGS. 46–48 is preferably releasably engaged with grasping forceps generally at the second end portion 470 of the resilient support structure 463 to position the device of FIGS. 46–48 within the urinary tract of the patient and/or to remove the device therefrom.

Another aspect of the present invention relates to an introducer 580 illustrated in FIGS. 55–59. The introducer 580 can be used as a conduit to pass a variety of devices into or through a body lumen or orifice to treat a variety of conditions. For example, the introducer 580 can be used to transurethrally position a variety of urological/gynecological devices, including the devices of the present invention such as device 310.

The introducer 580 is an elongate generally tubular structure having a first end 581, a second end 582, and a variable diameter central lumen 588 extending therethrough. The variable diameter feature of the central lumen 588 may be present along the entire length or along a portion of the length of the introducer 580. The introducer 580 also has an upper surface 583 and a lower surface 584.

The introducer 580 may also have a handle. The handle may be located at a variety of positions along the length of the introducer 580. Preferably, the handle is located at the second end 582 of the introducer 580.

The wall of the introducer 580 preferably has a longitudinally extending split 585, which extends from the first end 581 at least partially along the length of the wall of the introducer. Preferably, the longitudinally extending split 585 extends at least 2 cm from the first end 581 of the introducer 580. More preferably, the longitudinally extending split 585 extends from the first end 581 to the second end 582 of the introducer 580 as illustrated in FIG. 56. The split wall allows the introducer 580 to expand (FIG. 58) and contract or overlap (FIG. 59) relative to its resting state (FIG. 57). Expansion of the introducer 580 facilitates loading and deployment of the device 310 and minimizes distortion of the device 310 during loading and deployment thereof. To further facilitate expansion of the introducer 580, the second end 582 in the area of the split 585 can be chamfered approximately 0.1 cm by 45° at two places as illustrated at reference numeral 586 of FIG. 56. Contraction or overlapping of the walls of the introducer 580, such as in response as radially inwardly directed urethral forces during transurethral placement, minimizes the profile of the introducer 580, thereby minimizing urethral trauma and patient discomfort. In addition, the edges of the introducer 580 are smoothed using conventional manufacturing techniques to minimize urethral trauma.

The introducer 580 can be made from a variety of materials, including polymers such as cellulosics, polyesters and polyolefins. A preferred cellulosic material for the introducer 580 is Cellulose Acetate Propionate (CAP), which can be purchased from Eastman under the brand name "Tenite."

The first end 581 of the introducer 580 also preferably has an atraumatic tip 587 as illustrated in FIG. 55. The atraumatic tip 587 can be formed from a variety of materials, including the material used to construct the introducer 580. Preferably, the atraumatic tip 587 is formed with silicone, such as room temperature vulcanizing silicone (NuSil MED 2000). Small holes can be drilled into the first end 581 of the introducer 580 to facilitate attachment of the atraumatic tip 587, such as when the atraumatic tip 587 is formed with silicone.

The dimensions of the introducer 580 largely depend on anatomic considerations, the size of the device being inserted through the introducer, and the material used to construct the introducer. The length of the upper surface 583 of the introducer 580 is preferably approximately 8.0–14.0 cm, more preferably about 12.0 cm. As illustrated in FIG. 55, the length of the upper surface 583 is preferably greater than the length of the lower surface 584 so that the first end 581 slopes upwardly relative to the longitudinal axis of the introducer 580 at approximately a 30° angle. The outer diameter of the introducer 580 is preferably approximately 0.50–1.0 cm, more preferably about 0.70 cm. The wall thickness of the introducer 580 is preferably approximately 0.30–1.0 mm, more preferably about 0.50 mm. If an atraumatic tip 587 is included, it preferably extends longitudinally along the wall of the introducer 580 approximately 1.0–3.0 mm, more preferably about 2.0 mm.

An alternative nonsurgical or minimally invasive procedure for positioning an intraurethral device within the flow path between the bladder and the introitus to maintain urinary continence in a patient using the introducer 580 is generally accomplished as follows. For convenience, the following positioning and removal procedures will be described with reference to device 310. One of skill in the art will recognize, however, that these positioning and removal procedures can be used with a variety of devices, including the other embodiments of the present invention described in the subject application.

The urethral length is measured from the bladder to the introitus using a balloon measurement catheter or other conventional measuring techniques. A device for maintaining urinary continence, such as device 310, is selected by the physician. If necessary, the tubular body 312 is cut to length by the physician based on the patient's measured urethral length so that the length of the device 310 is tailored to the individual patient. Preferably the tubular body 312 is cut so that the length of the device 310 is preferably approximately 0.2–1.0 cm less than the measured urethral length, more preferably about 0.6 cm less than the measured urethral length.

A releasable engaging device, such as grasping forceps 225, is passed through the lumen 588 of the introducer 580 to releasably engage the device 310. The forceps can releasably engage the distal end 320 of the tubular body 312 directly, or can engage a gripping boss/tab or a tether 357 attached to the tubular body.

Using a coupling device, preferably a releasable coupling device such as a C-clip 291, the shaft 295 of the forceps 225 is attached to the shaft of a locating device having an expandable tip, such as a balloon catheter 290. Preferably, the shaft 295 of the forceps 225 is attached to the shaft 292 of the balloon catheter 290 so that the shoulder 293 of the balloon 294 of the balloon catheter 290 is separated by a distance "L" from the proximal end 331 of the first anchor 314 of the device 310 as illustrated in FIGS. 60–65. The distance "L" can be varied depending on where in the urinary tract the physician wants to anchor the device 310. The distance "L" may also be adjusted if a non-releasable coupling device is used, such as by sliding the shaft of the balloon catheter relative to the shaft of the forceps. Preferably "L" is approximately 1–7 mm, more preferably about 3–7 mm so that the first anchor 314 of the device 310 lodges in the bladder neck and/or proximal urethra.

Figure 60:
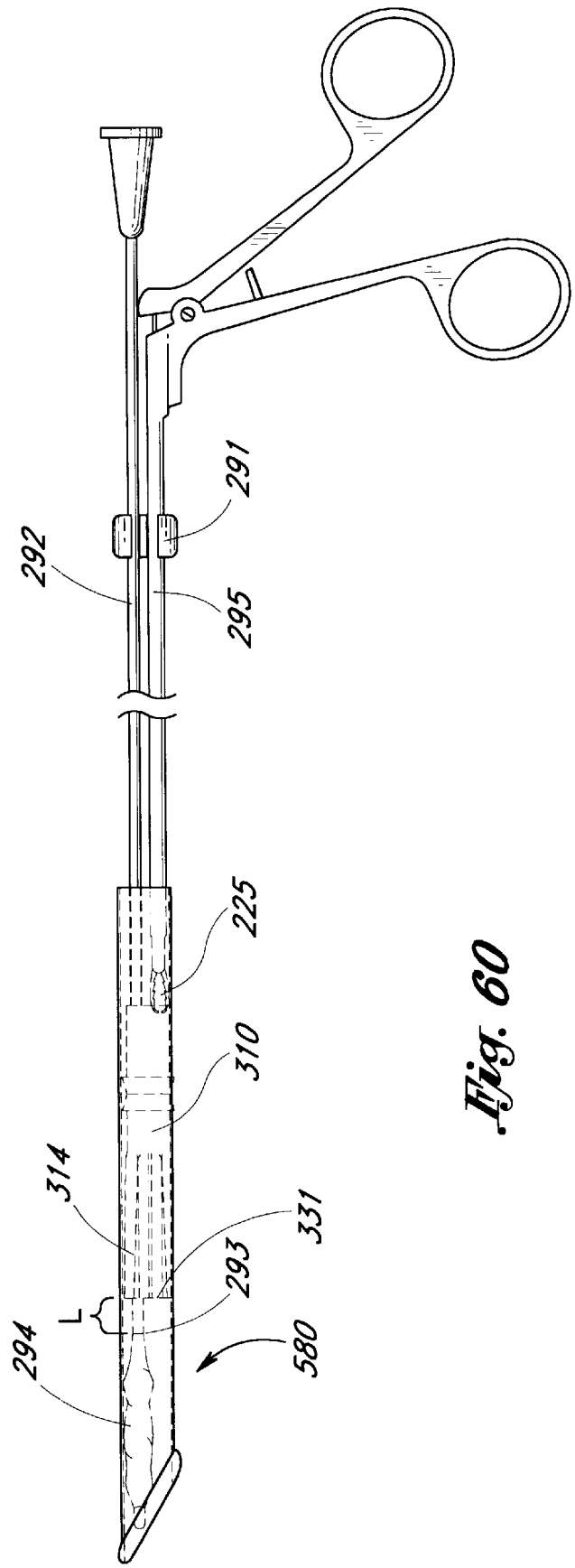
FIG. 60 is an assembled side view showing the device for maintaining urinary continence, balloon catheter, and grasping forceps inserted into the introducer.

The outside of the device 310 and balloon catheter 290 are lubricated with a water soluble lubricant, such as K-Y jelly and gently withdrawn into the introducer 580 as illustrated in FIG. 60. The introducer 580 is then passed into the urethra 40 so that the first end 581 of the introducer 580 extends into the bladder 30 as illustrated in FIG. 61.

Figure 61:
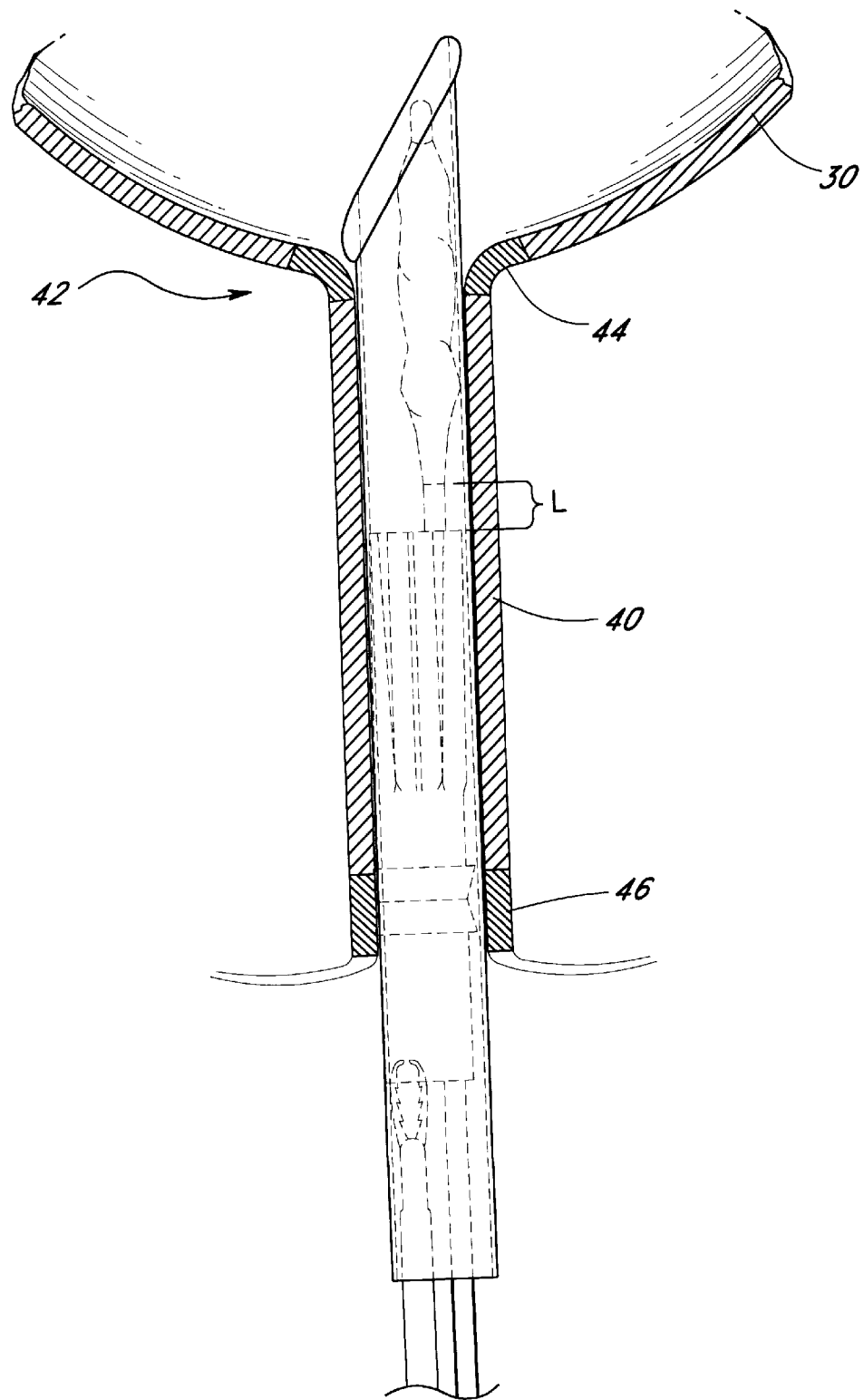
FIG. 61 is a schematic cross-sectional view showing the loaded introducer inserted into the urethra and bladder.

FIG. 61 also schematically illustrates the external urethral sphincter 46 and the internal urethral sphincter 44. In the female anatomy, the external urethral sphincter is difficult to distinguish. In the subject application, the external urethral sphincter is understood to include the urethral tissue immediately proximal to the urethral introitus. In the subject application, the internal urethral sphincter is intended to include the tissue at the urethro-vesical junction, also referred to as the bladder neck.

Figure 62:
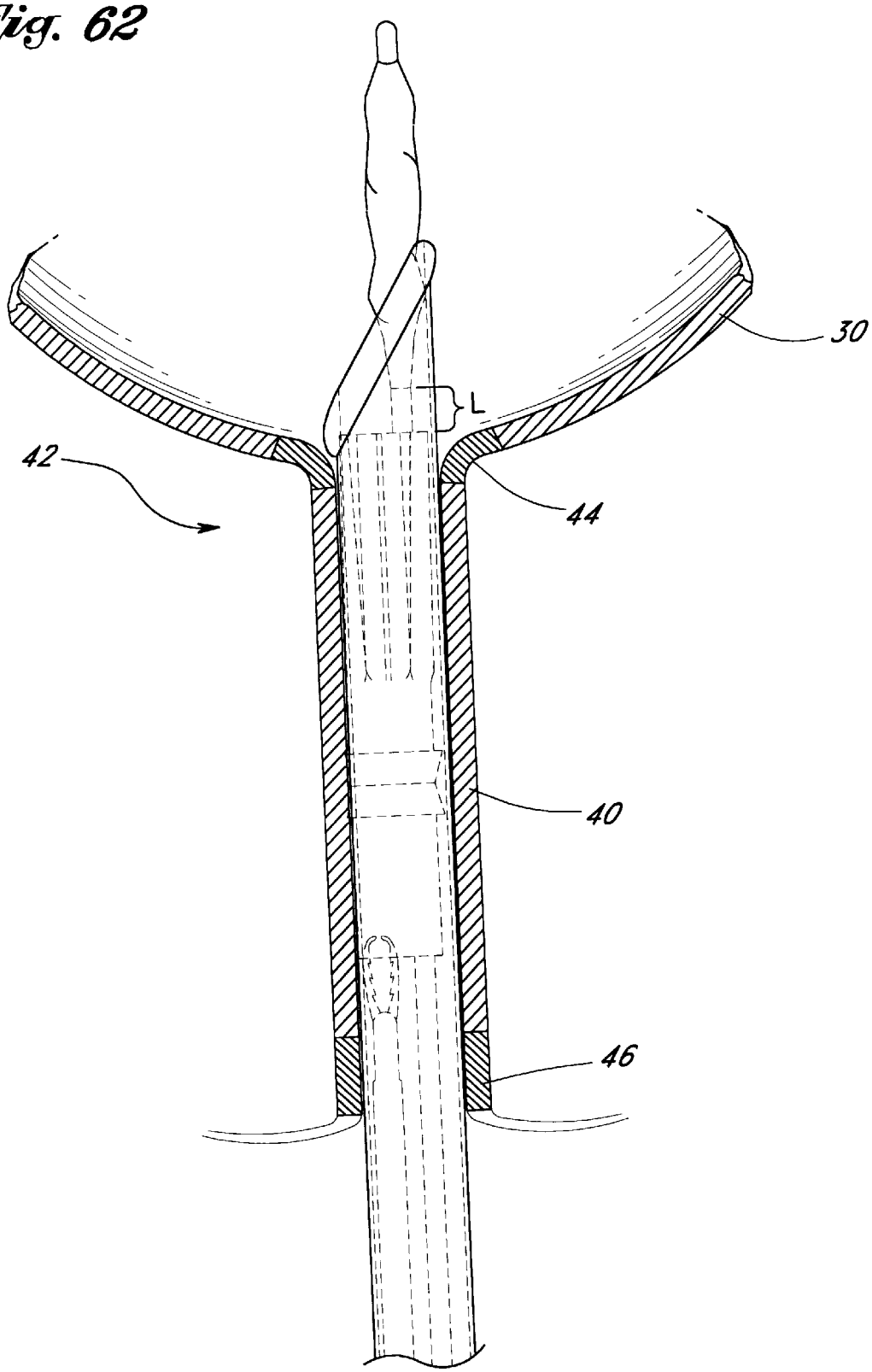
FIG. 62 is a schematic cross-sectional view showing the balloon catheter being advanced out of the introducer and into the bladder.
Figure 63:
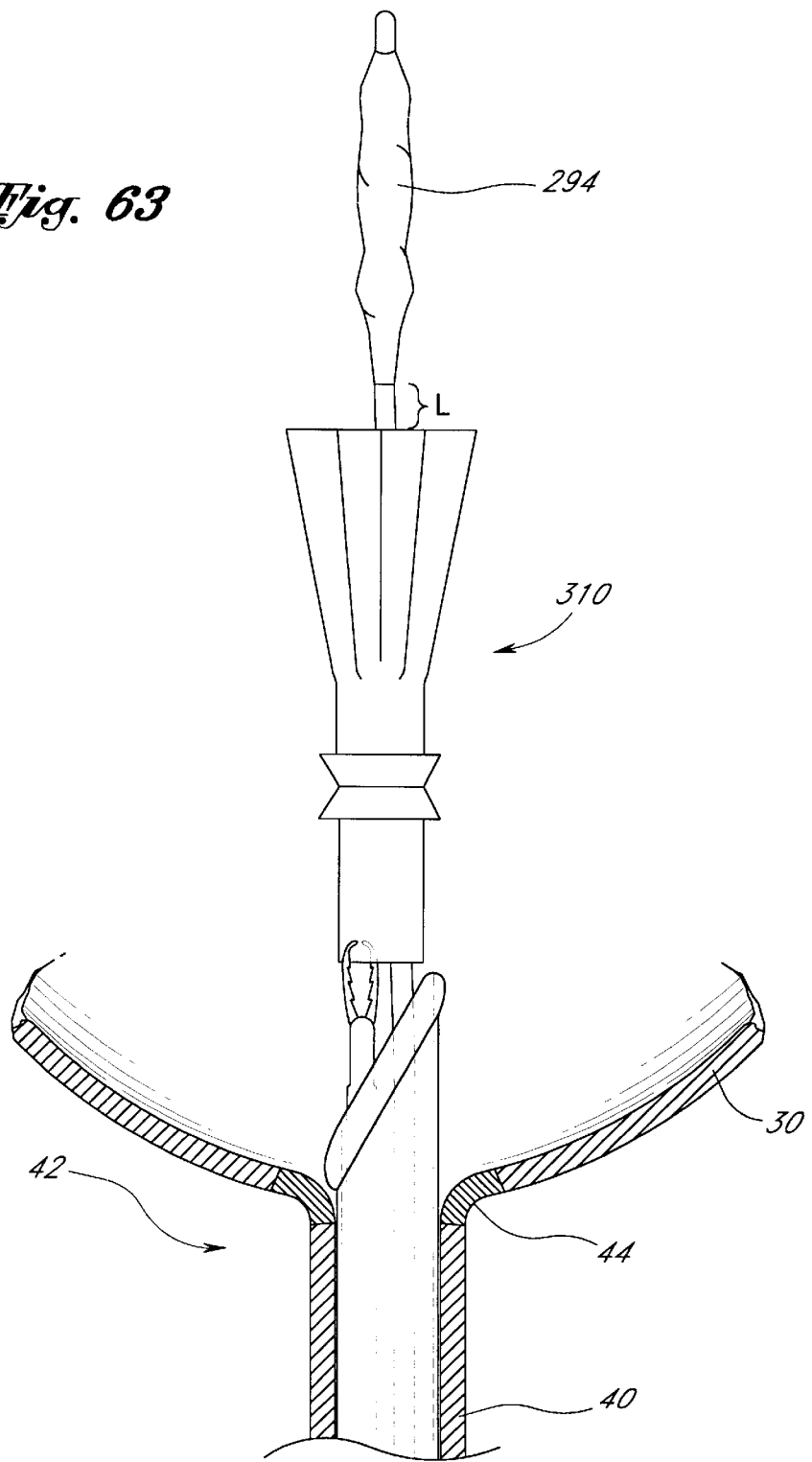
FIG. 63 is a schematic cross-sectional view showing the balloon catheter and device for maintaining urinary continence being displaced from the introducer into the bladder.
Figure 64:
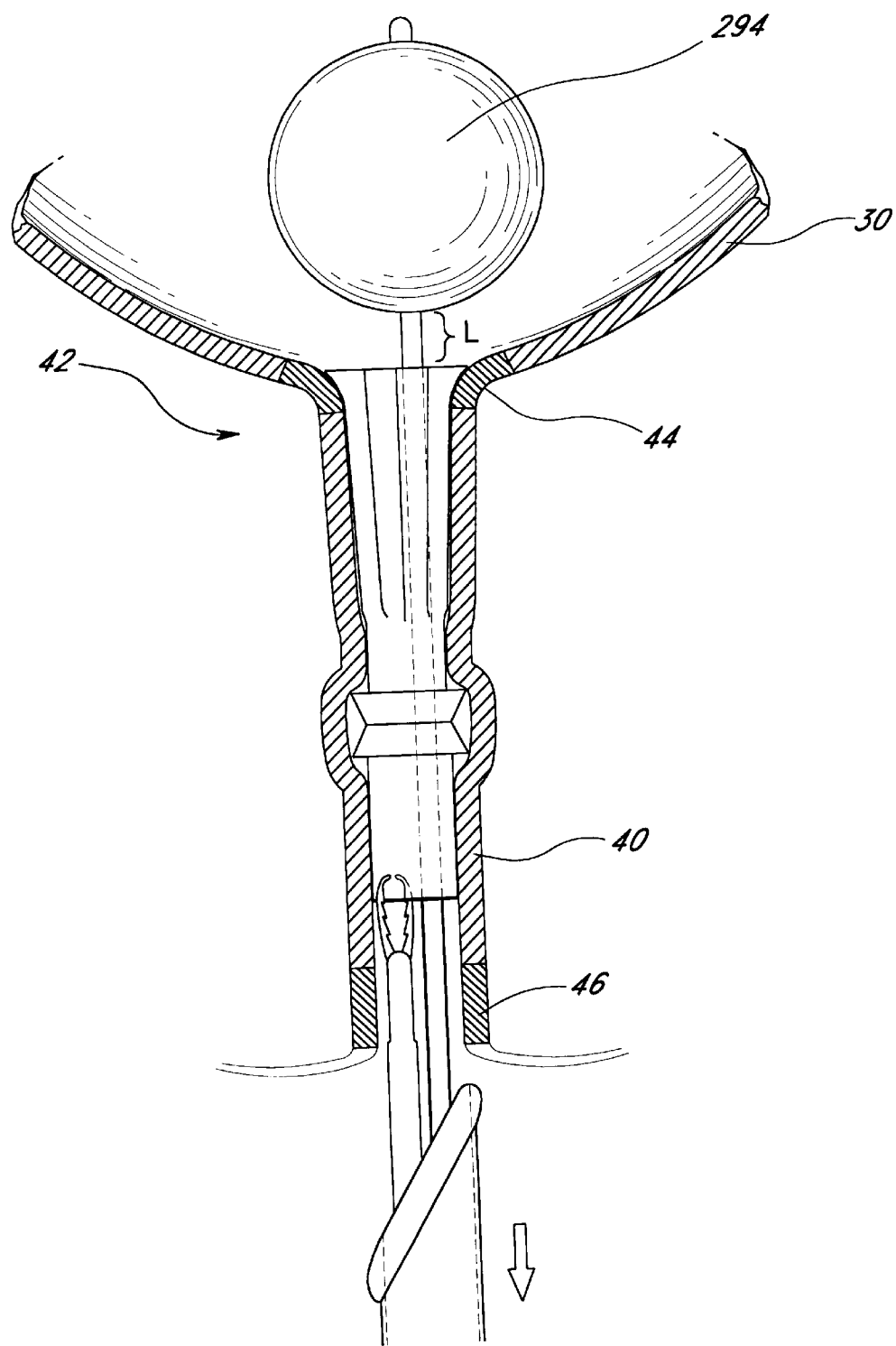
FIG. 64 is a schematic cross-sectional view showing the introducer being withdrawn from the urethra and the balloon being inflated within the bladder.
Figure 65:
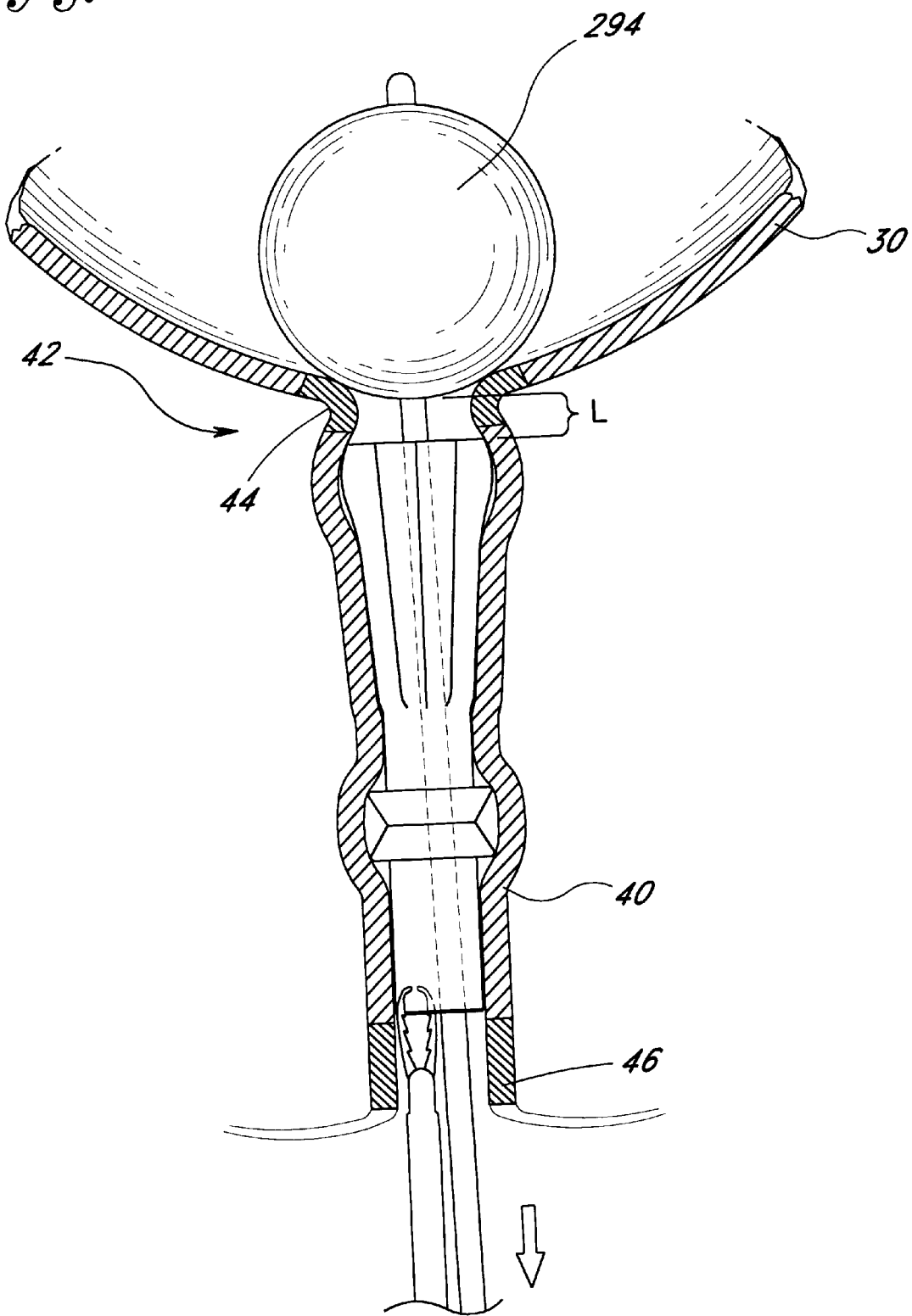
FIG. 65 is a schematic cross-sectional view showing withdrawal of the coupled grasping forceps and balloon catheter with the inflated balloon contacting the bladder neck.

FIGS. 62–63 illustrate the device 310 and balloon catheter 290 being carefully pushed out of the introducer 580 and into the bladder 30. As illustrated in FIG. 64, the introducer 580 is then withdrawn from the urethra 40 and the balloon 294 is inflated using conventional inflation media, such as water. The coupled grasping forceps 225 and balloon catheter 290 are then carefully withdrawn until the inflated balloon 294 contacts the bladder neck 42 a illustrated in FIG. 65. At this point, the proximal end 331 of the first anchor 314 resides within the bladder neck and/or proximal urethra the pre-selected distance "L" from the shoulder 293 of the inflated balloon 294.

The balloon 294 is deflated and the shaft 295 of the grasping forceps 225 is decoupled from the shaft 292 of the balloon catheter 290. The balloon catheter 290 is removed from the patient, the device 310 is released from the grasping forceps 225, and the grasping forceps are removed from the patient, leaving the device 310 properly positioned within the urinary tract of the patient as illustrated in FIG. 66. If a non-releasable coupling device is used, the balloon 294 is deflated, the device 310 is released from the grasping forceps 225, and the coupled grasping forceps 225 and balloon catheter 290 are removed simultaneously from the patient, leaving the device 310 properly positioned within the urinary tract of the patient.

Preferably the entire device 310 is positioned within the urethra. The device 310 is held in place due to the natural compliance of the urethra 40. Optionally, the position of the device 310 can be confirmed using well-known radiologic methods, such as in those embodiments which include radiopaque markers 355.

Figure 68:
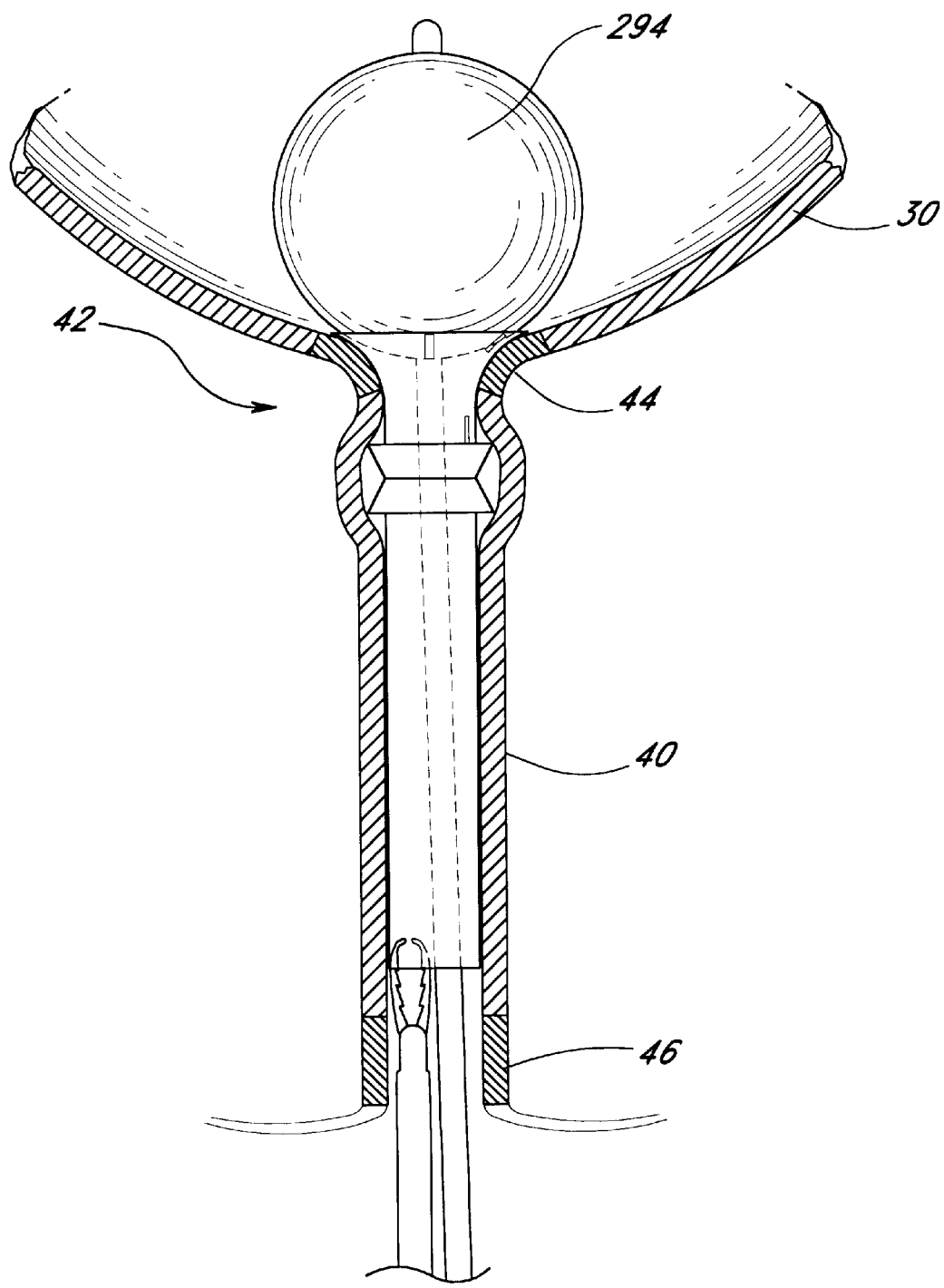
FIG. 68 is a schematic cross-sectional view showing the device for maintaining urinary continence being placed in an alternative position in the urinary tract.
Figure 69:
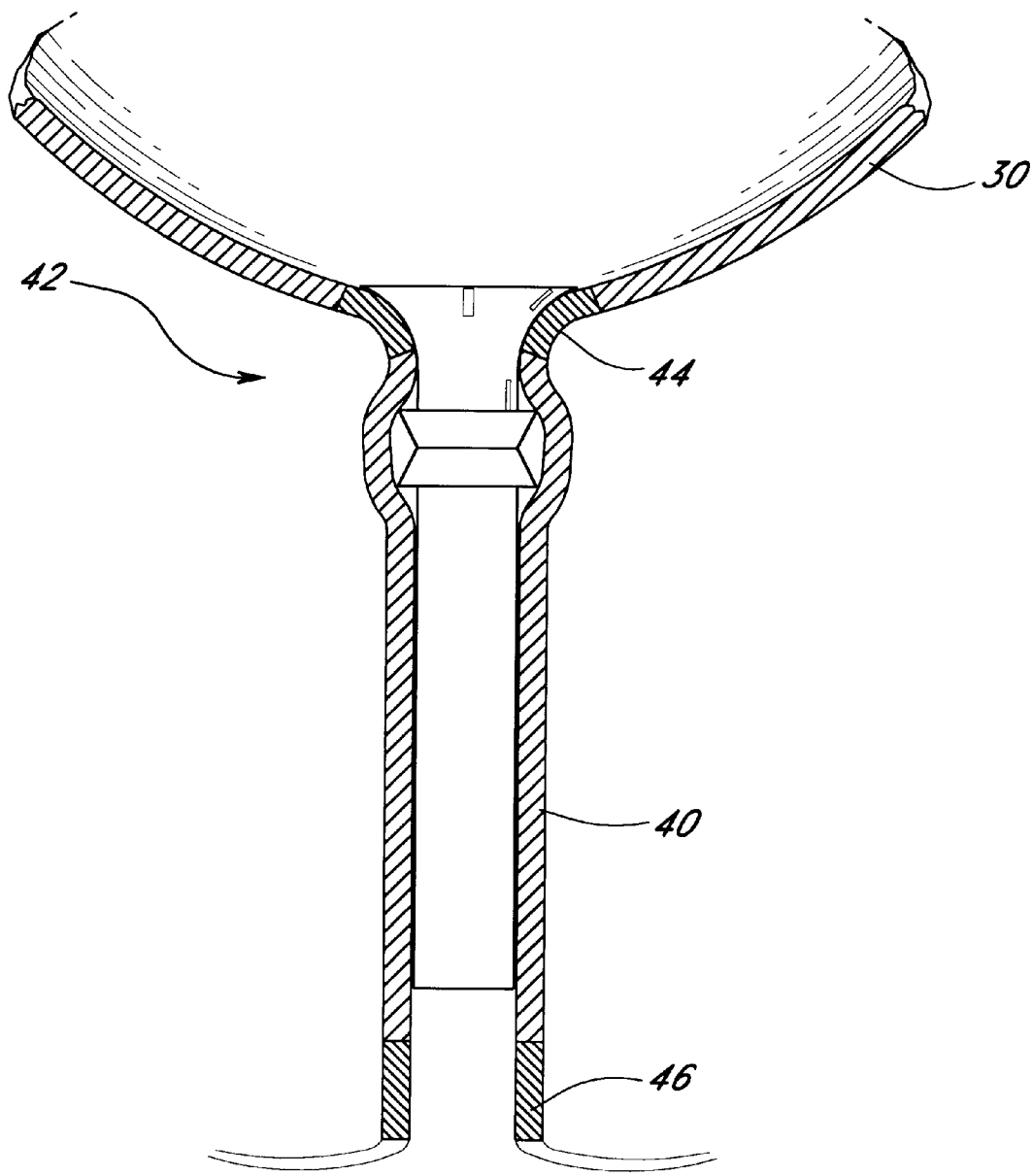
FIG. 69 is a schematic cross-sectional view showing the device for maintaining urinary continence positioned within the urinary tract after removal of the balloon catheter and grasping forceps illustrated in FIG. 68.

FIGS. 68–69 illustrate the device 310 placed in an alternative position. The position of the device in the urinary tract is related to a number of factors, such as the etiology of the patient's incontinence and the type of device being using to treat the patient. As illustrated by comparing FIGS. 65–66 to FIGS. 68–69, by varying the position of the shoulder 293 of the balloon 294 in relation to the proximal end 331 of the first anchor 314 prior to coupling the shaft 295 of the grasping forceps 225 to the shaft 292 of the balloon catheter 290, the physician can accurately place the device 310 in any of several desired positions in the urinary tract.

The devices of the present invention, such as device 310, can also be positioned within the urinary tract fluoroscopically. As discussed above, after measuring the urethral length, the tubular body of the device is cut to length by the physician. The bladder is filled with contrast fluid. The distal end of the device 310 is releasably engaged using grasping forceps 225 as discussed above. The outside of the device 310 is lubricated with a water soluble lubricant, such as K-Y jelly and gently withdrawn into the introducer 580 as previously discussed. The introducer 580 is then passed into the urethra so that the proximal end of the introducer extends into the bladder as discussed above. The device 310 is carefully pushed out of the introducer 580 and into the bladder while still be held by the grasping forceps 225. The introducer is then withdrawn from the urethra. Under fluoroscopic control, the device 310 is then withdrawn into the urethra until the first anchor 314 is observed to be just within the bladder neck, which is indicated by visualizing an inward movement of the radiopaque markers 355 on the first anchor 314 as it enters the urethra. The device 310 is then released from the grasping forceps and the grasping forceps are removed from the patient, leaving the device properly positioned within the urinary tract. Optionally, the position of the device is reconfirmed fluoroscopically after having the patient perform a variety of conventional maneuvers and exercises, including those which increase abdominal pressure.

As needed, the devices of the present invention can be removed from the patient and replaced as previously discussed. Because the device 310 does not contain any protruding sharp or rigid elements, if an emergency arises, such as an obstruction, the device 310 can be pushed into the bladder using a conventional catheter, such as a Foley catheter without causing damage to the urethra or bladder. The device 310 can remain in the bladder without causing any complications until the patient is able to see their physician for removal and replacement of the device.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

What is claimed is:

1. An intraurethral device for maintaining urinary continence comprising:
   a tubular body having a proximal end, a distal end, and a central lumen extending therethrough, the tubular body having a shape which conforms to a urethra; and
   a first anchor attached to the tubular body, the first anchor conforming to a portion of a urethra to resist migration of the intraurethral device relative to the urethra;
      wherein the intraurethral device is made of a substantially compliant material so that the intraurethral device reversibly seals in response to anatomical forces affecting the urethra and bladder neck.

2. The intraurethral device of claim 1, wherein the first anchor is attached to the proximal end of the tubular body, the first anchor conforming to a portion of a proximal urethra to resist migration of the intraurethral device relative to the proximal urethra.

3. The intraurethral device of claim 1, wherein the tubular body of the intraurethral device reversibly seals in response to anatomical forces affecting the urethra and bladder neck.

4. The intraurethral device of claim 1, wherein the first anchor of the intraurethral device reversibly seals in response to anatomical forces affecting the urethra and bladder neck.

5. The intraurethral device of claim 1, wherein both the tubular body and the first anchor of the intraurethral device reversibly seal in response to anatomical forces affecting the urethra and bladder neck.

6. The intraurethral device of claim 1, further comprising a second anchor attached to the tubular body.

7. The intraurethral device of claim 1, wherein the proximal end of the tubular body has a first outer circumference and the distal end of the tubular body has a second outer circumference, and at least a portion of the tubular body between the proximal end and the distal end has a third outer circumference which is less than the first outer circumference and the second outer circumference.

8. The intraurethral device of claim 7, wherein the proximal end has a non-circular cross-sectional outer profile, and the first outer circumference is defined by the distance around a circle circumscribing the outer points of the cross-section of the proximal end.

9. The intraurethral device of claim 8, wherein the non-circular cross-sectional outer profile is a star shape.

10. The intraurethral device of claim 9, wherein the non-circular cross-sectional outer profile is oval.

11. The intraurethral device of claim 7, wherein the distal end has a non-circular cross-sectional outer profile, and the second outer circumference is defined by the distance around a circle circumscribing the outer points of the cross-section of the distal end.

12. The intraurethral device of claim 11, wherein the non-circular cross-sectional outer profile is a star shape.

13. The intraurethral device of claim 11, wherein the non-circular cross-sectional outer profile is oval.

14. The intraurethral device of claim 7, comprising proximal and distal annular flanges.

15. The intraurethral device of claim 14, wherein the proximal annular flange inclines radially outwardly proximal direction and the distal annular flange inclines radially outwardly in the distal direction.

16. The intraurethral device of claim 7, wherein the proximal end is flared.

17. The intraurethral device of claim 7, wherein the distal end is flared.

18. The intraurethral device of claim 3, wherein the first anchor has a greater cross sectional area than the tubular body.

19. The intraurethral device of claim 18, wherein the first anchor comprises a radially outwardly inclined surface.

20. The intraurethral device of claim 19, further comprising a second anchor.

21. The intraurethral device of claim 20, wherein the second anchor has a greater cross sectional area than the tubular body.

22. The intraurethral device of claim 21, wherein the first and second anchors are spaced apart from each other along the tubular body.

23. The intraurethral device of claim 22, wherein the first anchor inclines radially outwardly in the proximal direction and the second anchor inclines radially outwardly in the distal direction.

24. The intraurethral device of claim 23, wherein each of the first and second anchors is enlargeable from a first, collapsed configuration for transurethral placement, to a second, enlarged configuration.

25. The intraurethral device of claim 1, wherein the device is dimensioned to fit entirely within the urethra.

26. The intraurethral device of claim 7, wherein the device is dimensioned to fit entirely within the urethra.

* * * * *